(12) United States Patent
Kretser et al.

(10) Patent No.: US 10,034,920 B2
(45) Date of Patent: Jul. 31, 2018

(54) METHOD OF TREATMENT AND AGENTS USEFUL FOR SAME

(71) Applicant: PARANTA BIOSCIENCES LIMITED, Southbank, Victoria (AU)

(72) Inventors: David De Kretser, Surrey Hills (AU); Robyn O'Hehir, Parkville (AU)

(73) Assignee: PARANTA BIOSCIENCES LIMITED, Southbank, Victoria (AU)

( * ) Notice: Subject to any disclaimer, the term of this patent is extended or adjusted under 35 U.S.C. 154(b) by 0 days.

(21) Appl. No.: 14/383,254

(22) PCT Filed: May 17, 2013

(86) PCT No.: PCT/AU2013/000520
§ 371 (c)(1),
(2) Date: Sep. 5, 2014

(87) PCT Pub. No.: WO2013/170315
PCT Pub. Date: Nov. 21, 2013

(65) Prior Publication Data
US 2015/0023981 A1    Jan. 22, 2015

(30) Foreign Application Priority Data

May 17, 2012 (AU) ................ 2012902036
Dec. 11, 2012 (AU) ................ 2012905402

(51) Int. Cl.
A61K 38/22 (2006.01)
A61K 38/16 (2006.01)
A61K 38/55 (2006.01)
C07K 16/22 (2006.01)

(52) U.S. Cl.
CPC .............. *A61K 38/22* (2013.01); *A61K 38/55* (2013.01); *C07K 16/22* (2013.01); *C07K 2317/30* (2013.01)

(58) Field of Classification Search
None
See application file for complete search history.

(56) References Cited

U.S. PATENT DOCUMENTS

| 6,537,966 B1* | 3/2003 | Duan ................. | C07K 14/4703 435/252.3 |
| 2002/0028762 A1 | 3/2002 | Kojima | |
| 2005/0266519 A1* | 12/2005 | Mellor ............... | A61K 38/1709 435/69.1 |
| 2007/0248609 A1* | 10/2007 | De Kretser ........... | C07K 16/26 424/158.1 |
| 2008/0181869 A1 | 7/2008 | DeVore | |

FOREIGN PATENT DOCUMENTS

| WO | WO 2002/080952 A2 | 10/2002 |
| WO | WO 2004/022730 A1 | 3/2004 |
| WO | WO 2005/032578 A1 | 4/2005 |

OTHER PUBLICATIONS

Damman et al. Complement and renal transplantation: from donor to recipient. Transplantation. Apr. 15, 2008;85(7):923-7.*
Maeshima et al. Involvement of the activin-follistatin system in tubular regeneration after renal ischemia in rats. J Am Soc Nephrol. Aug. 2001;12(8):1685-95.*
Siedlecki et al. Delayed graft function in the kidney transplant. Am J Transplant. Nov. 2011;11(11):2279-96. Epub Sep. 19, 2011.*
Avlonitis et al. Early hemodynamic injury during donor brain death determines the severity of primary graft dysfunction after lung transplantation. Am J Transplant. Jan. 2007;7(1):83-90.*
Bittner et al., "Aprotinin decreases reperfusion injury and allograft dysfunction in clinical lung transplantation." *European Journal of Cardio-thoracic Surgery* 2006; 29: 210-215.
Boros and Bromberg, "New Cellular and Molecular Immune Pathways in Ischemia/Reperfusion Injury." *American Journal of Transplantation* 2006; 6: 652-658, Blackwell Munksgaard. USA.
Bunin et al., "The combinatorial synthesis and chemical and biological evaluation of a 1,4-benzodiazepine library." *Proc. Natl. Acad. Sci. USA* 1994; 91: 4708-4712. USA.
Cash et al., "Characterization of Follistatin-Type Domains and Their Contribution to Myostatin and Activin A Antagonism." *Molecular Endocrinology.* Jul. 2012; 26(7): 1167-1178.
Chalk et al., "Improved and automated prediction of effective siRNA." *Biochemical and Biophysical Research Communications* 2004; 319: 264-274.
Chong et al., "Toll-like receptor 4 mediates ischemia/reperfusion injury of the heart." *Cardiopulmonary Support and Physiology,* 2004; 128: 170-179.
Christie et al., "The Effect of Primary Graft Dysfunction on Survival after Lung Transplantation." *American Journal of Respiratory and Critical Care Medicine,* 2005; 171: 1312-1316.
Christie et al., "Impact of Primary Graft Failure on Outcomes Following Lung Transplantation." *Chest,* 2005; 127(1): 161-165.
Conrad et al., "In vitro selection methodologies to probe RNA function and structure." *Molecular Diversity,* 1995; 1: 69-78.
Cui et al., "OptiRNAi, an RNAi design tool." *Computer Methods and Programs in Biomedicine,* 2004; 75: 67-73.
de Perrot et al., "Ischemia-Reperfusion-induced Lung Injury." *American Journal of Respiratory and Critical Care Medicine,* 2003; 167: 490-511.
Dewitt et al., ""Diversomers": An approach to nonpeptide, nonoligomeric chemical diversity." *Proc. Natl. Acad. Sci. USA,* 1993; 90: 6909-6913. USA.

(Continued)

*Primary Examiner* — Shulamith H Shafer
(74) *Attorney, Agent, or Firm* — Foley & Lardner LLP

(57) ABSTRACT

The present invention relates generally to a method of modulating graft functionality. More specifically, the present invention relates to a method of downregulating the onset or progression of graft dysfunction by downregulating the functional level of activin. The method of the present invention is useful, inter alia, in the treatment and/or prophylaxis of conditions characterized by graft dysfunction, such as the primary graft dysfunction associated with organ transplantation.

9 Claims, 12 Drawing Sheets

(56) References Cited

OTHER PUBLICATIONS

Ding & Lawrence, "Statistical prediction of single-stranded regions in RNA secondary structure and application to predicting effective antisense target sites and beyond." *Nucleic Acids Research*, 2001; 29(5): 1034-1046. Oxford University Press.

Ding & Lawrence, "A statistical sampling algorithm for RNA secondary structure prediction." *Nucleic Acids Research*, 2003; 31(24): 7280-7301. Oxford University Press.

Ding et al., "Sfold web server for statistical folding and rational design of nucleic acids." *Nucleic Acids Research*, 2004; 32: W135-W141. Oxford University Press.

Egleton, "Bioavailability and Transport of Peptides and Peptide Drugs into the Brain." *Peptides*, 1997; 18(9): 1431-1439. USA.

Elbashir et al., "Analysis of gene function in somatic mammalian cells using small interfering RNAs." *Methods*, 2002; 26: 199-213.

Ellington, "Aptamers achieve the desired recognition." *Current Biology*, 1994; 4(5): 427-429.

Estenne & Hertz, "Bronchiolitis Obliterans after Human Lung Transplantation." *American Journal of Respiratory and Critical Care Medicine*, 2002; 166: 440-444.

Estenne et al., "Bronchiolitis Obliterans Syndrome 2001: An Update of the Diagnostic Criteria." *The Journal of Heart and Lung Transplantation*, 2002; 21: 297-310.

Hausenloy & Yellon, "The therapeutic potential of ischemic conditioning: an update." *Nature Reviews Cardiology*, Nov. 2011; 89: 519-629.

Jamieson and Friend, "Organ reperfusion and preservation." *Front Biosci.*, 2008; 13: 221-235.

Keutman et al., "The Role of Follistatin Domains in Follistatin Biological Action." *Molecular Endocrinology*, 2004; 18(1): 228-240. USA.

Khvorova et al., "Functional siRNAw and miRNA Exhibit Strand Bias." *Cell*, 2003; 115: 209-213.

Klein et al., "The Radioimmunoassay of Follicle-Stimulating Hormone (FSH)—Suppressing Protein (FSP): Stimulation of Bovine Granulosa Cell FSP Secretion by FSH*." *Endocrinology*, 1991; 128(2): 1048-1056. USA.

Klug & Famulok, "All you wanted to know about SELEX." *Molecular Biology Reports*, 1994; 20: 97-107. Kluwer Academic Publishers. Belgium.

Knight et al., "Development and application of a two-site enzyme immunoassay for the determination of 'total' activin-A concentrations in serum and follicular fluid." *Journal of Endocrinology*, 1996; 148: 267-279. (Abstract).

Kohler & Milstein, "Continuous cultures of fused cells secreting antibody of predefined specificity." *Nature*, 1975; 256: 495-499.

Kozower et al., "Immunotargeting of catalase to the pulmonary endothelium alleviates oxidative stress and reduces acute lung transplantation injury." *Nature Biotechnology*, 2003; 21: 392-398.

Lande et al., "Novel Insights into Lung Transplant Rejection by Microarray Analysis." *Proceedings of the American Thoracic Society*, 2007; 4: 44-51.

Langer, "New Methods of Drug Delivery." *Science*, 1990; 249: 1527-1533.

Laskowski et al., "Molecular and Cellular Events Associated with Ischemia/Reperfusion Injury." *Annals of Transplantation*, 2000; 5(4): 29-35.

Lato et al., "In vitro selection of RNA lectins: using combinatorial chemistry to interpret ribozyme evolution." *Chemistry & Biology*, 1995; 2: 291-303.

Lim et al., "Protective role of Coenzyme $Q^{10}$ in two models of rat lung injury." *ANZ J Surg*, 2010; 80: 265-270.

Lu et al., "Sequential Gene Expression Profiling in Lung Transplant Recipients With Chronic Rejection." *Chest*, 2006; 130(3): 847-854.

Ludlow et al., "A new 'total' activing B enzyme-linked immunosorbent assay (ELISA): development and validation for human samples." *Clinical Endocrinology*, 2009; 71: 867-873.

Mori et al., "Addition of a neutrophil elastase inhibitor to the organ flushing solution decreases lung reperfusion injury in rat lung transplantation." *European Journal of Cardio-thoratic Surgery*, 2007; 32: 791-795.

Ng et al., "Pulmonary ischemia-reperfusion injury: role of apoptosis." *European Respiratory Journal*, 2005, 25: 356-363. ERS Journals Ltd.

O'Connor et al., "Serum activing A and follistatin concentrations during human pregnancy: a cross-sectional and longitudinal study." *Human Reproduction*, 1999; 14(3): 827-832.

Okada et al., "Extinguishing Egr-1-dependent inflammatory and thrombotic cascades after lung transplantation." *The FASEB Journal*, 2001; 15: 2757-2759.

Reynolds et al., "Rational siRNA design for RNA interference." *Nature Biotechnology*, 2004; 22(3): 326-330.

Robertson et al., "The Isolation of Polypeptides With FSH Suppressing Activity From Bovine Follicular Fluid Which Are Structurally Different to Inhibin." *Biochemical and Biophysical Research Communications*, 1987; 149(2): 744-749.

Schwarz et al., "Asymmetry in the Assembly of the RNAi Enzyme Complex." *Cell*, 2003; 115: 199-208. Cell Press.

Shimoyama et al., "Aprotinin attenuated ischemia-reperfusion injury in an isolated rat lung after 18-hours preservation." *European Journal of Cardio-thoracic Surgery*, 2005; 28: 581-587.

Stein and Cohen, "Oligodeoxynucleotides as Inhibitors of Gene Expression: A Review." *Cancer Research* 1988; 48: 2659-2668.

Strüber et al., "Effects of exogenous surfactant instillation in clinical lung transplantation: A prospective, randomized trial." *The Journal of Thoracic and Cardiovascular Surgery*, 2007; 133: 1620-1625.

Sunose et al., "Effects of FK3311 on Pulmonary Ischemia-Reperfusion Injury in a Canine Model." *Journal of Surgical Research*, 2001; 95: 167-173.

Uphoff et al., "In vitro selection of aptamers: the dearth of pure reason." *Curr Opin Struct Biol*, 1996; 6: 281-287.

van der Krol et al., "Modulation of eukaryotic gene expression by complementary RNA or DNA sequences." *Biotechniques*, 1988; 6(10): 958-976.

van der Woude et al., "Preconditioning Strategies to Limit Graft Immunogenicity and Cold Ischemic Organ Injury." *Journal of Investigative Medicine*, 2004; 52(5): 323-329.

Venardos et al., "Reduced L-Arginine Transport Contributes to the Pathogenesis of Myocardial Ischemia-Reperfusion Injury." *Journal of Cell Biochemistry*, 2009; 108: 156-168.

Wallis et al., "A novel RNA motif for neomycin recognition." *Chemistry & Biology*, 1995; 2: 543-552.

Wang et al., "A Web-based design center for vector-based siRNA and siRNA cassette." *Bioinformatics*, 2004; 20(11): 1818-1820.

Wei et al., "Simulated Ischemia in Flow-Adapted Endothelial Cells Leads to Generation of Reactive Oxygen Species and Cell Signaling." *Circulation Research*, 1999; 85: 682-689.

Winnall et al., "Regulation of interleukin 1α, activing and inhibin by lipopolysaccharide in Sertoli cells from perpubertal rats." *Molecular and Cellular Endocrinology*, 2009; 307: 169-175.

Zhai et al., "Ischemia/Reperfusion Injury: The Role of CD26/Dipeptidyl-Peptidase-IV-Inhibition in Lung Transplantation." *Transplantation Proceedings*, 2006; 38: 3369-3371.

El-Aggan et al., "Study of Serum Activin A and Follistatin in Post Renal Transplant Patients: Correlation with Renal Hemodynamics, Graft Function and Survival." *Bul. Alex. Fac. Med.*, 2008; 44(4): 699-707.

Fakhfakh et al., "Administration of a Soluble Activin Type IIB Receptor Promotes the Transplantation of Human Myoblasts in Dystrophic Mice." *Cell Transplantation*, Mar. 2012; 21(7): 1419-1430.

Kanamoto et al., "Beneficial Effects of Follstatin in Hepatic Ischemia-Reperfusion Injuries in Rats." *Digestive Diseases and Sciences*, 2011; (published online Sep. 8, 2010) 56(4): 1075-1081.

International Search Report dated Jul. 1, 2013 in application No. PCT/AU2013/000520.

Supplementary European Search Report dated Sep. 25, 2015 in application No. EP 13 79 1008.

Hashimoto et al., "Difference between follistatin isoforms in the inhibition of activing signaling Activin neutralizing activity of

(56) References Cited

OTHER PUBLICATIONS follistatin isoforms is dependent on their affinity for activin," Cellular Signalling, vol. 12, pp. 565-571, 2000.
Harrison et al., "Antagonists of activing signaling: mechanisms and potential biological applications," Trends in Endocrinology and Metabolism, vol. 16, No. 2, pp. 73-78, Mar. 2005.
Tsuchida et al., "Identification and Characterization of a Novel Follistatin-like Protein as a Binding Protein for the TGF-β Family," The Journal of Biological Chemistry, vol. 275, No. 52, pp. 40788-40796, Sep. 2000.

\* cited by examiner

METHOD OF TREATMENT AND AGENTS USEFUL FOR SAME

FIELD OF THE INVENTION

The present invention relates generally to a method of modulating graft functionality. More specifically, the present invention relates to a method of downregulating the onset or progression of graft dysfunction by downregulating the functional level of activin. The method of the present invention is useful, inter alia, in the treatment and/or prophylaxis of conditions characterised by graft dysfunction, such as the primary graft dysfunction associated with organ transplantation.

BACKGROUND OF THE INVENTION

Bibliographic details of the publications referred to by author in this specification are collected alphabetically at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Organ transplantation has become an established therapy for selected patients with end-stage organ dysfunction. As a result the number of patients referred for transplantation continues to increase thereby exacerbating a chronic donor organ shortage problem and leading to the use of more "marginal" organs that would otherwise have been declined during previous years. However, in addition to the problems of organ rejection, this being the most widely publicized complication of organ transplantation, there occurs another serious complication which often precedes rejection, this being the onset of graft dysfunction. This condition can both lead to failure of the organ and exacerbate immunological rejection of the organ. The incidence of this complication has been exacerbated by virtue of the use of organs which, in previous years, would have been regarded as unsuitable for use as a transplant. Still further, primary graft dysfunction occurs despite significant advances in organ handling, storage and preservation, with an incidence of between 10% and 12% and with an associated risk of mortality at 30 days of between 42% and 63%, making it the leading cause of early death after transplantation (Christie et al. 2005, *Am J Respir Crit Care Med* 171:1312-1316; Christie et al. 2005, *Chest* 127:161-165).

Primary graft dysfunction or failure is a form of allograft ischemia-reperfusion injury that typically occurs within 72 hours of transplantation and is exacerbated by acute and chronic conditions that compromise the donor allograft. In the setting of lung transplantation, for example, it is particularly common and is characterised by hypoxemia, substantial alveolar oedema and non-specific alveolar damage, similar to what is characteristic of Acute Respiratory Distress Syndrome (ARDS) (Christie et al. 2005 supra; de Perrot et al. 2003, *Am J Respir Crit Care Med* 167:490-511). The pathophysiological changes that are associated with lung ischemia-reperfusion are complex and involve time-dependent modulation of various oxidative stress, proinflammatory and prothrombotic pathways that ultimately result in cellular injury and death. In addition to lung, other solid transplant organs including kidney, liver and heart undergo similar ischemia-reperfusion injury related changes in preparation for transplantation that result in the establishment of a proinflammatory state that may be detrimental to graft survival (Boros and Bromberg 2006, *Am J Transplant* 6:652-658; Jamieson and Friend 2008, *Front Biosci* 13:221-235; Laskowski et al. 2000, *Ann Transplant* 5:29-35; van der Woude et al. 2004, *J Investig Med* 52:323-329).

Lung endothelial cells, alveolar monocytes/macrophages and neutrophils have been shown to contribute to the generation of toxic reactive oxygen species (ROS) during periods of ischemia and reperfusion and these oxygen-derived free radicals play a major role in precipitating cellular injury and pulmonary damage (de Perrot et al. 2003, supra; Ng et al. 2005, *Eur Respir J* 25:356-363). During non-hypoxic lung ischemia, as would be present during the initial phase of donor lung storage, pulmonary endothelial cells appear to be a major source of ROS generation due to activation of the NADPH oxidase system via a distinct mechanism that involves mechanotransduction initiated by the lack of vascular flow (Wei et al. 1999, *Circ Res* 85:682-689). As well as generating ROS that contribute to ischemia-reperfusion injury of lung transplant tissue, gene expression studies using RNA extracted from bronchioalveolar lavage (BAL)-derived cells post transplantation have demonstrated that primary graft dysfunction is associated with the upregulation of multiple genes associated with inflammation, apoptosis, cellular growth and fibrosis (Lande et al. 2007, *Proc Am Thorac Soc* 4:44-51; Lu et al. 2006, *Chest* 130:847-854). This process similarly occurs in other types of donor tissues.

Since the pathological consequences of ischemia-reperfusion injury have been identified as the primary cause of graft failure, much recent focus has been on donor lung assessment and handling as a means of preserving function and minimizing subsequent ischemia-reperfusion injury. The development of several lung preservation solutions such as the intracellular type solutions that rely on high $K^+$, low $Na^+$ and the extracellular type solutions (low $K^+$, high $Na^+$), with and without additives such as Dextran 40, glucose and raffinose has allowed for better donor preservation and extension of ischemic times up to 12 hours with excellent donors (de Perrot et al. 2003, supra). As an extension of this preservation process, it has been determined that subtle variations in volume, pressure and temperature of the perfusion solution can also minimize ischemic damage and lead to better outcomes (de Perrot et al. 2003, supra).

A number of other pharmacological strategies targeting the donor tissue either prior to retrieval and/or during storage have been shown to moderate the extent of ischemia-reperfusion injury after both experimental and clinical transplantation. Instillation of exogenous surfactant to donor tissue just prior to retrieval has been shown to have a protective effect (Struber et al. 2007, *J Thorac Cardiovasc Surg* 133:1620-1625). Immunotargeting of the antioxidant enzyme catalase to the endothelium via conjugation to anti-PECAM antibodies was shown to reduce oxidative stress and subsequent ischemia-reperfusion injury and also prolonged the acceptable cold ischemia storage time of grafts (Kozower et al. 2003, *Nat Biotechnol* 21:392-398). Inhibition of protease activity by inclusion of the Kunitz type serine protease inhibitor aprotinin to the preservation solution has been shown to attenuate ischemia-reperfusion injury in both animal models (Shimoyama et al. 2005, *Eur J Cardiothorac Surg* 28:581-587) and in clinical transplantation (Bittner et al. 2006, *Eur J Cardiothorac Surg* 29:210-215). Addition of a neutrophil elastase inhibitor directly to the preservation solution prior to storage for 16 hours led to reduced ischemia-reperfusion injury and improved tissue function (Mori et al. 2007, *Eur J Cardiothorac Surg* 32:791-

795). Direct addition of the dipeptidyl peptidase (DPP) IV inhibitor AB 192 to the preservation solution prior to storage for 18 hours reduced ischemia-reperfusion injury to the tissue and allowed for successful transplantation (Zhai et al. 2006, *Transplant Proc* 38:3369-3371). As an alternate approach to reducing tissue damage, Okada et al. (*FASEB J* 15:2757-2759, 2001) showed that treating donor tissue with an antisense oligonucleotide to block expression of the hypoxia-induced transcription factor Egr-1 inhibited induction of Egr-1 and its downstream target genes such as IL-1β, tissue factor and plasminogen activator inhibitor-1, resulting in marked improvement in graft function and recipient survival. Overall, these previous studies demonstrate that it is technically feasible to pre-treat donor tissue via several pharmacological strategies in order to attempt to mitigate ischemia-reperfusion injury after transplantation.

Nevertheless, although significant advances in donor organ preservation, surgical techniques, immunosuppressive therapies and anti-infective strategies over the last 20 years have been associated with improved graft outcomes in the short to medium term, disappointingly, these have not translated into improved long term outcomes. This is particularly true in the case of lung transplantation where despite often acceptable early lung function being achieved, chronic rejection associated allograft dysfunction, which clinically manifests as Bronchiolitis Obliterans Syndrome (BOS), occurs in 40% of lung transplant recipients (LTR) at 2 years and leads to mortality rates as high as 50% at 5 years (Estenne and Hertz 2002, *Am J Respir Crit Care Med* 166:440-444; Estenne et al. 2002, *J Heart Lung Transplant* 21:297-310). BOS is the leading cause of long term mortality in lung transplant recipients and may be significantly contributed to both directly and indirectly by early events related to ischemia-reperfusion injury (Estenne and Hertz 2002, supra; Estenne et al. 2002, supra). Accordingly, there is an ongoing need to develop better methods for the treatment and handling of organs during the harvesting and transplantation process.

In work leading up to the present invention it has been determined that the complex physiological processes which contribute to the onset and progression of graft dysfunction can be retarded by either downregulating the functionality of activin or upregulating follistatin levels.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

One aspect of the present invention is directed to a method of downregulating the onset or progression of mammalian graft tissue dysfunction said method comprising downregulating the functional level of activin in said tissue.

In another aspect there is provided a method of downregulating the onset or progression of mammalian tissue dysfunction said method comprising upregulating the functional level of follistatin in said tissue.

In still another aspect there is provided a method of downregulating the onset or progression of mammalian graft tissue dysfunction, which graft tissue is lung, said method comprising downregulating the functional level of activin or upregulating the functional level of follistatin in said tissue.

In yet another aspect there is provided a method of downregulating the onset or progression of mammalian graft tissue dysfunction, which graft tissue is kidney, said method comprising downregulating the functional level of activin or upregulating the functional level of follistatin in said tissue.

In still yet another aspect there is provided a method of downregulating the onset or progression of mammalian graft tissue dysfunction, which graft tissue is liver, said method comprising downregulating the functional level of activin or upregulating the functional level of follistatin in said tissue.

In a further aspect there is provided a method of downregulating the onset or progression of mammalian graft tissue dysfunction, which graft tissue is heart, said method comprising downregulating the functional level of activin or upregulating the functional level of follistatin in said tissue.

In still a further aspect there is provided a method of downregulating the onset or progression of mammalian graft tissue dysfunction said method comprising pretreating said tissue with an effective amount of an inhibitor of activin for a time and under conditions sufficient to downregulate activin functionality.

In another aspect there is provided a method of downregulating the onset or progression of mammalian graft tissue dysfunction said method comprising pretreating said tissue with an effective amount of follistatin.

Yet, another aspect of the present invention provides a method for the prophylactic and/or therapeutic treatment of a condition characterised by mammalian graft tissue dysfunction said method comprising downregulating the functional level of activin or upregulating the functional level of follistatin in said tissue.

In yet still another aspect there is provided the use of follistatin or an inhibitor of activin in the manufacture of a medicament for the treatment of mammalian graft tissue dysfunction.

Still yet another aspect of the invention is directed to follistatin an inhibitor of activin functionality for use in the therapeutic or prophylactic treatment of graft tissue dysfunction.

DETAILED DESCRIPTION OF THE INVENTION

Figure 1:
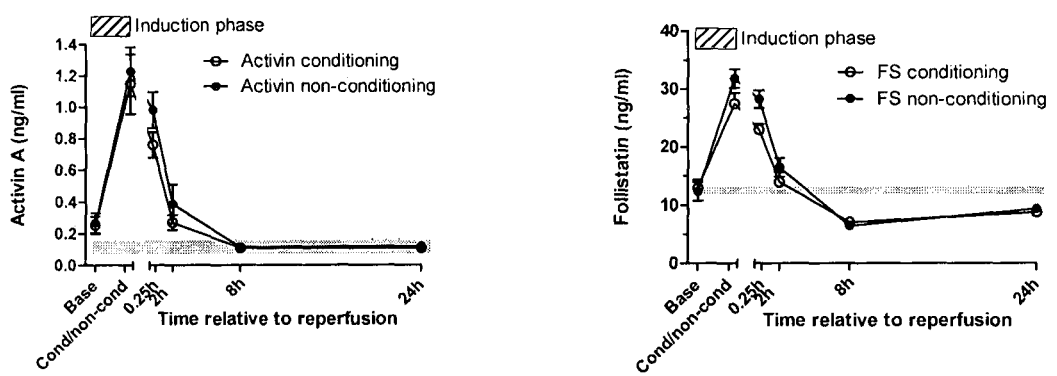
FIG. 1: Plasma concentrations of activin A (left panel) and follistatin (right panel) in lung transplant patients. Profiles are presented as mean±SEM, with open circles indicating those patients randomized to ischemic conditioning and closed circles those patients randomized to the usual care protocol. The shaded bar in each panel indicates the normal range for both activin A and follistatin, and the hatched box indicates the period of surgery/reperfusion during the transplantation procedure.

The present invention is predicated, in part, on the determination that by either downregulating the functional level of activin or increasing follistatin levels in a graft tissue, the incidence or severity of graft dysfunction can be reduced. This development is particularly exciting since it now provides a routine means of effectively reducing the incidence of graft dysfunction, this not having been achievable to date. To date, the development of transplantation technology has tended to focus on maintaining the viability of the cells of an organ subsequently to its harvesting and prior to transplantation or on the development of means to suppress host versus graft or graft versus host immunological rejection. However, the notion of modulating the physiological processes which are occurring in a harvested organ has not been extensively pursued. To this end, by controlling this process there is provided a means of supporting the host's tolerance induction process, to the extent that it may occur.

In light of the complexity of the physiological processes involved in the onset of graft dysfunction, the notion of a whole organ approach to regulating these processes has not been seriously pursued to date. There have been attempts made to treat the inflammation aspect of this condition by the use of steroids. However, this has had only limited success, thereby highlighting the fact that in order to reduce the incidence of graft dysfunction, it is necessary to regulate more than just isolated aspects of the processes which occur during graft dysfunction. The determination that activin inhibition and/or follistatin administration can achieve this outcome has now provided an unexpected and previously unavailable means for routinely and effectively improving graft functionality, and thereby its prospects for successful transplantation, by reducing the incidence and/or severity of graft dysfunction.

Accordingly, one aspect of the present invention is directed to a method of downregulating the onset or progression of mammalian graft tissue dysfunction said method comprising downregulating the functional level of activin in said tissue.

In another aspect there is provided a method of downregulating the onset or progression of mammalian tissue dysfunction said method comprising upregulating the functional level of follistatin in said tissue.

The present invention is predicated on treating graft tissue in order to reduce the incidence of dysfunction. By "graft tissue" is meant a tissue which is either intended to be or has been transplanted from a donor source to a recipient source. That is, the graft may still be located in situ (i.e. has not yet been harvested) or it may already have been harvested but not yet transplanted. Even after transplant, said tissue is still referred to as the "graft".

In general, the donor of the tissue and the recipient of the tissue will both be mammals. However, reference to "graft tissue" should also be understood to extend to tissues which have been generated in vitro, such as tissues which are developed from stem cells or cell lines. Such tissues may be, for example, grown on three-dimensional scaffolds. It should be understood that the subject tissue may be all or part of an organ or tissue (e.g. skin, foetal tissue). Examples of graft tissues to which the present invention may be applied include, but are not limited to lung, heart, liver, kidney, pancreas, spleen, limbs or parts thereof (such as fingers, toes, hands, ears or other appendages), bowel or skin. However, said tissue does not include within its scope single cell suspensions which are sometimes the subject of transfer to a recipient, such as bone marrow, stem cells or blood.

The tissue may be donated from any suitable source. It should also be understood that the tissue may have undergone some form of other treatment or manipulation either prior to or subsequently to the application of the method of the invention. For example, the tissue may have been stored for a period of time or otherwise treated, such as in order to preserve its viability. The tissue may also have undergone genetic manipulation or other form of treatment or manipulation, either before or after harvesting from its source, to modulate its structure or functioning. In another example, it may be necessary to treat the tissue in, order to minimise the possibility of the transfer of host derived pathogens. It would be appreciated, that tissues destined for transplantation currently undergo certain standard treatments, such as lowering of their temperature, immersion or perfusion with solutions which support viability or the like. Accordingly, the tissues of the present invention are envisaged to nevertheless also be subject to these standard handling techniques at any suitable point in time relative to the application of the method of the invention.

It should also be appreciated that the subject tissue may be autologous/syngeneic, allogeneic or xenogeneic relative to the recipient mammal. For example, the subject graft tissue could be autologous if it was generated from the recipient's own cells which were identified, isolated and/or differentiated into a tissue or organ ex vivo and transplanted back into the individual from which they were originally harvested. However, it should be understood that the present invention nevertheless extends to the use of tissues derived from any other suitable source where the subject tissues exhibit the same major histocompatibility (MHC) profile as the individual who is the subject of treatment. Accordingly, such tissues are effectively autologous in that they would not result in the histocompatibility problems which are normally associated with the transplanting of tissues exhibiting a foreign MHC profile. To this end, although these tissues would not lead to problems of immunological rejection, they would, nevertheless, still suffer from the complications linked to their harvesting and the onset of graft dysfunction—the onset of these complications being largely unrelated to the MHC haplotype of the graft. Such tissue should be understood as falling within the definition of "autologous". For example, under certain circumstances it may be desirable, necessary or of practical significance that the subject tissue is isolated from a genetically identical twin. The tissue may also have been grown in vitro and engineered to exhibit the desired MHC profile. The use of such tissue overcomes the difficulties which are inherently encountered in the context of tissue and organ transplants.

However, where it is not possible or feasible to isolate or generate autologous graft tissue, which is currently the case for most patients, it may be necessary to utilise an allogeneic graft. "Allogeneic" grafts are those which are isolated from the same species as the subject being treated but which exhibit a different MHC haplotype. Although the use of such a graft in the context of therapeutics would likely necessitate the use of immunosuppression treatment, this problem can nevertheless be minimised by use of a graft which exhibits an MI-IC profile exhibiting similarity to that of the subject being treated, such as a graft which has been isolated/generated from a relative such as a sibling, parent or child. The present invention should also be understood to extend to xenogeneic transplantation. That is, the graft which is introduced into a patient is isolated from a species other than the species of the subject being treated. This may occur, for example, where one administers pancreatic tissue isolated from a pig or organs isolated from non-human primates.

In one embodiment, said graft tissue is lung, kidney, liver or heart.

According to this embodiment there is provided a method of downregulating the onset or progression of mammalian graft tissue dysfunction, which graft tissue is lung, said method comprising downregulating the functional level of activin or upregulating the functional level of follistatin in said tissue.

In another embodiment there is provided a method of downregulating the onset or progression of mammalian graft tissue dysfunction, which graft tissue is kidney, said method comprising downregulating the functional level of activin or upregulating the functional level of follistatin in said tissue.

In yet another embodiment there is provided a method of downregulating the onset or progression of mammalian graft tissue dysfunction, which graft tissue is liver, said method comprising downregulating the functional level of activin or upregulating the functional level of follistatin in said tissue.

In still another embodiment there is provided a method of downregulating the onset or progression of mammalian graft tissue dysfunction, which graft tissue is heart, said method comprising downregulating the functional level of activin or upregulating the functional level of follistatin in said tissue.

Reference to "mammalian" or "mammal" should be understood as a reference to humans, primates, livestock animals (e.g. horses, cattle, sheep, pigs, donkeys), laboratory test animals (e.g. mice, rats, guinea pigs), companion animals (e.g. dogs, cats) and captive wild animal (e.g. kangaroos, deer, foxes). Preferably, the mammal is a human or a laboratory test animal. Even more preferably, the mammal is a human.

As detailed hereinbefore, the method of the present invention achieves downregulation of the onset or progression of graft tissue dysfunction. Reference to "dysfunction" should be understood as a reference to the occurrence of cellular injury, such as cell death, and/or aberrant or unwanted cellular functionality.

Without limiting the present invention to any one theory or mode of action, primary graft dysfunction usually occurs as a result of graft ischemia. This form of injury is a common problem in the context of organ transplantation. In general, this type of injury and the onset of graft dysfunction occur within 72 hours of transplantation. In addition to the damage which this dysfunction causes to the functioning of the organ itself, often leading to failure of the organ and subsequently patient death, it can also exacerbate immunological rejection of the organ.

Still without limiting the invention in any way, dysfunction can be characterised by one or more of the onset of oxidative stress, inflammation and thrombosis which directly lead to cellular injury and death. The endothelial cells, monocytes/macrophages and other non-specific granulocytic immune cells are activated and can contribute to the generation of reactive oxygen species. This can, in fact, occur during non-hypoxic ischemia, which is evident in the initial phases of donor organ storage. Upregulation of reactive oxygen species is usually also associated with the upregulation of the expression of genes associated with inflammation, apoptosis, cellular growth and fibrosis. IL-8 expression is often increased, thereby increasing neutrophil recruitment and phospholipases are activated leading to the generation of lipids which constrict the vasculature and increase capillary permeability. This extensive network of physiological responses should be understood to fall within the scope of "unwanted cellular functionality" as detailed above. It would be appreciated that most of these processes are normal physiological processes but which, in a circumstance such as the harvesting of an organ for transplantation, are unwanted since they ultimately lead to cellular injury of the donor tissue and damage to the functionality of the organ. Still without limiting the present invention, it has been found that the inflammatory aspects of this dysfunction can in fact occur during both the cold ischemic preservation period shortly after harvesting the organ and after reperfusion once the organ has been transplanted into the recipient.

Reference to "dysfunction" should therefore be understood as a reference to any one or more aspects of this process as it occurs in the context of organs which have been harvested. To this end, it should be understood that reference to "downregulating" the onset or progression of said dysfunction should be understood as a reference to reducing the level of any one or more aspects of said dysfunction, to the extent that it has already commenced, or preventing, reducing or delaying the onset of said dysfunction. Reduction in the level, of severity of said dysfunction may be partial, in that some lower level of dysfunction does continue to occur or otherwise cannot be reversed, or it may be total in that the dysfunction is either entirely prevented from its onset or, to the extent that it has already commenced, it is eliminated. In many circumstances, even a partial reduction in the onset or progression of dysfunction may nevertheless be desirable outcomes, since it may at least reduce the extent and alter the nature of the reduction in organ functionality. For example, where an organ may previously have been expected to entirely fail, which in the context of liver, heart or lung failure would usually lead to the death of the patient, it may be possible to reduce the dysfunction sufficiently that total organ failure is prevented, even if some level of dysfunction nevertheless occurs and could not be fully prevented. It is generally preferred that the downregulation of dysfunction is complete rather than partial, although whether or not this is achievable will depend on the circumstances of the particular situation, such as how early the method of the present invention was applied to the harvested organ subsequently to its removal from the donor.

Reference to "activin" should be understood as a reference to an activin β subunit dimer. The subject dimer may be a homodimer or a heterodimer of the activin β subunits, these including $\beta_A$, $\beta_B$, $\beta_C$, $\beta_D$ and $\beta_E$. Reference to the subunits should be understood to include reference to any isoforms which may arise from alternative splicing of activin β mRNA or mutant or polymorphic forms of activin β. Reference to "activin β" is not intended to be limiting and should be read as including reference to all forms of activin β including any protein encoded by the activin β subunit genes, any subunit polypeptide such as precursor forms which may be generated, and any β protein, whether existing as a monomer, multimer or fusion protein. Multimeric protein forms of activin include, for example, the homodimeric activin B ($\beta_B$-$\beta_B$) or the heterodimeric activin AB ($\beta_A$-$\beta_B$), activin BC ($\beta_B$-$\beta_C$), activin BD ($\beta_B$-$\beta_D$), activin BE ($\beta_B$-$\beta_E$) activin A ($\beta_A$$\beta_A$), activin AC ($\beta_A$$\beta_C$), activin AD ($\beta_A$$\beta_D$), activin AE ($\beta_A$$\beta_E$), activin C ($\beta_C$$\beta_C$), activin CD ($\beta_C$$\beta_D$), activin CE ($\beta_C$$\beta_E$), activin D ($\beta_D$$\beta_D$), activin DE ($\beta_D$$\beta_E$) and activin E ($\beta_E$$\beta_E$) proteins. Preferably, said activin molecule is activin A or activin B.

In terms of downregulating the "functional level" of activin or upregulating the "functional level" of follistatin, this should be understood to mean the level of activin or follistatin which is functional. It would be appreciated by the person of skill in the art that the functional level of activin can be downregulated either by reducing absolute levels of activin or by antagonising the functional activity of activin such that its effectiveness is decreased. Even the partial antagonism of activin may act to reduce, although not necessarily eliminate, the functional effectiveness of activin. Increasing the functional level of follistatin should be understood to have a converse meaning. For example one can increase the absolute levels of follistatin or one may increase its bioavailability, such as by increasing its half-life.

In terms of achieving the downregulation of activin, means for achieving this objective would be well known to the person of skill in the art and include, but are not limited to:

(i) Introducing into a cell a proteinaceous or non-proteinaceous molecule which downregulates the transcriptional and/or translational regulation of a gene, wherein this gene may be the activin gene or functional portion thereof or some other gene or gene region (e.g. promoter region) which directly or indirectly modulates the expression of the activin gene; or (ii) Introducing a proteinaceous or non-proteinaceous molecule which functions as an antagonist to the activin expression product.

In terms of achieving upregulation of follistatin, this can also be achieved by any suitable method including administering the follistatin protein itself or introducing a proteinaceous or non-proteinaceous molecule which upregulates the transcription and/or translation of the follistatin gene.

The proteinaceous molecules described above may be derived from any suitable source such as natural, recombinant or synthetic sources and includes fusion proteins or molecules which have been identified following, for example, natural product screening. The reference to non-proteinaceous molecules may be, for example, a reference to a nucleic acid molecule or it may be a molecule derived from natural sources, such as for example natural product screening, or may be a chemically synthesised molecule. The present invention contemplates small molecules capable of acting as antagonists. Antagonists may be any compound capable of blocking, inhibiting or otherwise preventing activin from carrying out its normal biological function. Antagonists include monoclonal antibodies and antisense nucleic acids which prevent transcription or translation of activin genes or mRNA in mammalian cells. Modulation of expression may also be achieved utilising antigens, RNA, ribosomes, DNAzymes, aptamers, antibodies or molecules suitable for use in cosuppression. Suitable antisense oligonucleotide sequences (single stranded DNA fragments) of activin may be created or identified by their ability to suppress the expression of activin. The production of antisense oligonucleotides for a given protein is described in, for example, Stein and Cohen, 1988 (*Cancer Res* 48:2659-2668) and van der Krol et al., 1988 (*Biotechniques* 6:958-976). Antagonists also include any molecule that prevents activin interacting with its receptor.

In the context of antibodies, the present invention envisages the use of any suitable form of antibody including catalytic antibodies or derivatives, homologues, analogues or mimetics of said antibodies. Such antibodies may be monoclonal or polyclonal and may be selected from naturally occurring activin or its subunits or may be specifically raised to the activin dimer or its monomers (herein referred to as the "antigen"). In the case of the latter, the antigen may first need to be associated with a carrier molecule. Alternatively, fragments of antibodies may be used such as Fab fragments or Fab'$_2$ fragments. Furthermore, the present invention extends to recombinant and synthetic antibodies and to antibody hybrids. A "synthetic antibody" is considered herein to include fragments and hybrids of antibodies. The antigen can also be used to screen for naturally occurring antibodies.

Both polyclonal and monoclonal antibodies are obtainable by immunization with the antigen or derivative, homologue, analogue, mutant, or mimetic thereof and either type is utilizable therapeutically. The methods of obtaining both types of sera are well known in the art. Polyclonal sera are less preferred but are relatively easily prepared by injection of a suitable laboratory animal with an effective amount of the antigen, or antigenic parts thereof, collecting serum from the animal, and isolating specific sera by any of the known immunoabsorbent techniques. Although antibodies produced by this method are utilizable, they are generally less favoured because of the potential heterogeneity of the product.

The use of monoclonal antibodies is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example Douillard and Hoffman 1981, Basic Facts about Hybridomas, in *Compendium of Immunology* Vol II, ed. by Schwartz; Kohler and Milstein 1975, *Nature* 256:495-499; Kohler and Milstein 1976, *Eur J Immun* 6:511-519).

Preferably, the antibody of the present invention specifically binds the antigen. By "specifically binds" is meant high avidity and/or high affinity binding of an antibody to a specific antigen. Antibody binding to its epitope on this specific antigen is stronger than binding of the same antibody to any other epitope, particularly those that may be present in molecules in association with, or in the same sample, as the specific antigen of interest. Antibodies that bind specifically to a polypeptide of interest may be capable of binding other polypeptides at a weak, yet detectable, level (e.g., 10% or less of the binding shown to the polypeptide of interest). Such weak binding, or background binding, is readily discernible from the specific antibody binding to the polypeptide of interest, e.g. by use of appropriate controls.

The proteinaceous and non-proteinaceous molecules referred to, above, are herein collectively referred to as "modulatory agents". To the extent that it is sought to decrease activin activity or increase follistatin activity, said modulatory agent is preferably:

(i) Follistatin. This may be administered either as a protein or its overexpression may be induced in vivo such as via the adenovirus mediated system described by Takabe et al. 2003 (*Hepatology* 38:1107-1115).

(ii) Any agent that upregulates the expression or functioning of the α subunit of inhibin. The α subunit can dimerise with the β subunits of activin to form inhibin, thereby effectively downregulating activin levels.

(iii) Inhibin. This molecule can bind to β-glycan and inhibit the actions of activin via its receptor. See for example the mechanism described by Xu et al. 1995 (*J Biol Chem* 270:6308-6313) or the use of the Smad7 antagonist (Bernard et al. 2004, *Molecule Endocrinol* 18:606-623).

(iv) Any agent that upregulates levels of $\beta_C$ since this results in the formation of the inactive AC form of activin.

(v) Activin neutralising antibody. For example, as described in Poulaki et al. 2004 (*Am J Pathol* 164: 1293-1302).

(vi) Activin mutants which inhibit native activin from binding to its receptor. For example, as described in Harrison et al. 2004, (*J Biol Chem* 279:28036-28044), or modifications of the prodomain of the activin propeptide (see Makanji Y et al. 2011 Generation of a specific activin antagonist by modification of the activin propeptide. *Endocrinol* 152:3758-3768).

(vii) Transfection or treatment with a mutant activin receptor which prevents normal activin signalling or a soluble activin receptor which acts as a competitive inhibitor. See for example, the system described by Maeshima et al. 2004 (*Endocrinology* 145:3739-3745).

(viii) An activin antisense oligonucleotide.

(ix) A thrombin antagonist such as lepirudin.

In this regard, reference to "follistatin" should be read as including reference to all forms of follistatin including, by way of example, the three protein cores and six molecular weight forms which have been identified as arising from the alternatively spliced mRNAs FS315 and FS288. Accordingly, it should also be understood to include reference to any isoforms which may arise from alternative splicing of follistatin mRNA or mutant or polymorphic forms of follistatin. It should still further be understood to extend to any protein encoded by the follistatin gene, any subunit polypeptide, such as precursor forms which may be generated, and any follistatin protein, whether existing as a monomer, multimer or fusion protein. An analogous definition applies to "inhibin".

Other forms of follistatin which are suitable for use in the present invention include:

(i) Wild-type follistatin (FS), comprising an N-terminal domain (ND) followed by three follistatin domains (FSD1, FSD2 and FSD3) with a heparin-binding sequence located in FSD1 (amino acid sequence positions 72-86), and all known isoforms thereof.

(ii) Wild-type follistatin-like 3 protein (FSTL3), which is also known as follistatin-related gene product (FLRG) and follistatin-related protein (FSRP), comprising an N-terminal domain (N3D) followed by two follistatin-like 3 domains (FS3D1 and FS3D2), and all known isoforms thereof.

(iii) Follistatin analogue having the structure ND-FSD1-FSD2 (i.e. wild-type minus FSD3).

(iv) Analogues of (i) and (iii) above with FSD1 substituted by FSD1', where FSD1' represents FSD1 with heparin-binding site removed.

(v) Analogues of (i) and (iii) above with FSD1 substituted by FSD1*, where FSD1* represents FSD1 with sequence prior to and including the heparin-binding sequence removed.

(vi) Hybrid forms of (i) and (iii) above where at least one of the domains is substituted by a corresponding FSTL3 domain N3D, FS3D1 and FS3D2.

(vii) Hybrid forms of (ii) above where at least one of the domains is substituted by a corresponding FS domain ND, FSD1, FSD1', FSD1* and FSD2.

(viii) Any of the above proteins modified by one or more deletions, insertions and/or mutations in ND, N3D, FSD1, FSD1', FSD1*, FS3D1, FSD2, FS3D2, and FSD3 provided the modified protein functions as an activin antagonist.

(Jennifer N. Cash, Elizabeth B. Angerman, Henry T. Keutmann, and Thomas B. Thompson 2012 Characterization of Follistatin-Type Domains and Their Contribution to Myostatin and Activin A Antagonism. *Mol Endocrinol*, 26(7): 1167-1178; Henry T. Keutmann, Alan L. Schneyer and Yisrael Sidis 2004 The Role of Follistatin Domains in Follistatin Biological Action. *Mol Endocrinol*, 18(1):228-240)

Screening for the modulatory agents hereinbefore defined can be achieved by any one of several suitable methods including, but in no way limited to, contacting a cell comprising the activin gene or functional equivalent or derivative thereof with an agent and screening for the downregulation of activin protein production or functional activity, downregulation of the expression of a nucleic acid molecule encoding activin or downregulation of, the activity or expression of a downstream activin cellular target. Detecting such downregulation can be achieved utilising techniques such as Western blotting, electrophoretic mobility shift assays and/or the readout of reporters of activin activity such as luciferases, CAT and the like.

It should be understood that the activin gene or functional equivalent or derivative thereof may be naturally occurring in the cell which is the subject of testing or it may have been transfected into a host cell for the purpose of testing. Further, the naturally occurring or transfected gene may be constitutively expressed—thereby providing a model useful for, inter alia, screening for agents which down regulate activin activity, at either the nucleic acid or expression product levels, or the gene may require activation—thereby providing a model useful for, inter alia, screening for agents which up-regulate activin expression. Further, to the extent that an activin nucleic acid molecule is transfected into a cell, that molecule may comprise the entire activin gene or it may merely comprise a portion of the gene such as the portion which regulates expression of the activin product. For example, the activin promoter region may be transfected into the cell which is the subject of testing. In this regard, where only the promoter is utilised, detecting modulation of the activity of the promoter can be achieved, for example, by ligating the promoter to a reporter gene. For example, the promoter may be ligated to luciferase or a CAT reporter, the downregulation of expression of which gene can be detected via modulation of fluorescence intensity or CAT reporter activity, respectively. In another example, the subject of detection could be a downstream activin regulatory target, rather than activin itself. Yet another example includes activin binding sites ligated to a minimal reporter.

These methods provide a mechanism for performing high throughput screening of putative modulatory agents such as the proteinaceous or non-proteinaceous agents comprising synthetic, combinatorial, chemical and natural libraries.

These methods will also facilitate the detection of agents which bind either the activin nucleic acid molecule or expression product itself or which modulate the expression of an upstream molecule, which upstream molecule subsequently downregulates activin expression or expression product activity. Accordingly, these methods provide a mechanism of detecting agents which either directly or indirectly modulate activin expression and/or activity.

The agents which are utilised in accordance with the method of the present invention may take any suitable form. For example, proteinaceous agents may be glycosylated or unglycosylated, phosphorylated or dephosphorylated to various degrees and/or may contain a range of other molecules used, linked, bound or otherwise associated with the proteins such as amino acids, lipid, carbohydrates or other peptides, polypeptides or proteins. Similarly, the subject non-proteinaceous molecules may also take any suitable form. Both the proteinaceous and non-proteinaceous agents herein described may be linked, bound otherwise associated with any other proteinaceous or non-proteinaceous molecules. For example, in one embodiment of the present invention said agent is associated with a molecule which permits its targeting to a localised region.

The subject proteinaceous or non-proteinaceous molecule may act either directly or indirectly to downregulate the expression of activin or the activity of the activin expression product. Said molecule acts directly if it associates with the activin nucleic acid molecule or expression product to modulate expression or activity, respectively. Said molecule acts indirectly if it associates with a molecule other than the activin nucleic acid molecule or expression product which other molecule either directly or indirectly downregulates the expression or activity of the activin nucleic acid molecule or expression product, respectively. Accordingly, the method of the present invention encompasses the regulation of activin nucleic acid molecule expression or expression product activity via the induction of a cascade of regulatory steps.

The term "expression" refers to the transcription and translation of a nucleic acid molecule. Reference to "expression product" is a reference to the product produced from the transcription and translation of a nucleic acid molecule.

"Derivatives" of the molecules herein described (for example activin A, activin B, follistatin or other proteinaceous or non-proteinaceous agents) include fragments, parts, portions or variants from either natural or non-natural sources. Non-natural sources include, for example, recombinant or synthetic sources. By "recombinant sources" is meant that the cellular source from which the subject molecule is harvested has been genetically altered. This may occur, for example, in order to increase or otherwise enhance the rate and volume of production by that particular cellular source. Parts or fragments include, for example, active regions of the molecule. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in a sequence has been removed and a different residue inserted in its place. Additions to amino acid sequences include fusions with other peptides, polypeptides or proteins, as detailed above.

Derivatives also include fragments having particular epitopes or parts of the entire protein fused to peptides, polypeptides or other proteinaceous or non-proteinaceous molecules. For example, follistatin, or derivative thereof may be fused to a molecule to facilitate its localisation to a particular site. Analogues of the molecules contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues.

Derivatives of nucleic acid sequences which may be utilised in accordance with the method of the present invention may similarly be derived from single or multiple nucleotide substitutions, deletions and/or additions including fusion with other nucleic acid molecules. The derivatives of the nucleic acid molecules utilised in the present invention include oligonucleotides, PCR primers, antisense molecules, molecules suitable for use in cosuppression and fusion of nucleic acid molecules. Derivatives of nucleic acid sequences also include degenerate variants.

A "variant" or "mutant" should be understood to mean molecules which exhibit at least some of the functional activity of the form of molecule (e.g. follistatin) of which it is a variant or mutant. A variation or mutation may take any form and may be naturally or non-naturally occurring.

A "homologue" is meant that the molecule is derived from a species other than that which is being treated in accordance with the method of the present invention. This may occur, for example, where it is determined that a species other than that which is being treated produces a form of follistatin, for example, which exhibits similar and suitable functional characteristics to that of the follistatin which is naturally produced by the subject undergoing treatment.

Chemical and functional equivalents should be understood as molecules exhibiting any one or more of the functional activities of the subject molecule, which functional equivalents may be derived from any source such as being chemically synthesised or identified via screening processes such as natural product screening. For example chemical or functional equivalents can be designed and/or identified utilising well known methods such as combinatorial chemistry or high throughput screening of recombinant libraries or following natural product screening. Antagonistic agents can also be screened for utilising such methods.

For example, libraries containing small, organic molecules may be screened, wherein organic molecules having a large number of specific parent group substitutions are used. A general synthetic scheme may follow published methods (e.g., Bunin et al. 1994, *Proc Natl Acad Sci USA* 91:4708-4712; DeWitt et al. 1993, *Proc Natl Acad Sci USA* 90:6909-6913). Briefly, at each successive synthetic step, one of a plurality of different selected substituents is added to each of a selected subset of tubes in an array, with the selection of tube subsets being such as to generate all possible permutation of the different substituents employed in producing the library. One suitable permutation strategy is outlined in U.S. Pat. No. 5,763,263.

There is currently widespread interest in using combinational libraries of random organic molecules to search for biologically active compounds (see for example U.S. Pat. No. 5,763,263). Ligands discovered by screening libraries of this type may be useful in mimicking or blocking natural ligands or interfering with the naturally occurring ligands of a biological target. By use of techniques, such as that disclosed in U.S. Pat. No. 5,753,187, millions of new chemical and/or biological compounds may be routinely screened in less than a few weeks. Of the large number of compounds identified, only those exhibiting appropriate biological activity are further analysed.

With respect to high throughput library screening methods, oligomeric or small-molecule library compounds capable of interacting specifically with a selected biological agent, such as a biomolecule, a macromolecule complex, or cell, are screened utilising a combinational library device which is easily chosen by the person of skill in the art from the range of well-known methods, such as those described above. In such a method, each member of the library is screened for its ability to interact specifically with the selected agent. In practicing the method, a biological agent is drawn into compound-containing tubes and allowed to interact with the individual library compound in each tube. The interaction is designed to produce a detectable signal that can be used to monitor the presence of the desired interaction. Preferably, the biological agent is present in an aqueous solution and further conditions are adapted depending on the desired interaction. Detection may be performed for example by any well-known functional or non-functional based method for the detection of substances.

The present invention is also directed to useful aptamers. In one embodiment, an aptamer is a compound that is selected in vitro to bind preferentially to another compound (in this case the identified proteins), in one aspect, aptamers are nucleic acids or peptides. Random sequences can be readily generated from nucleotides or amino acids (naturally occurring and/or synthetically made) in large numbers but of course they need not be limited to these. In another aspect, the nucleic acid aptamers are short strands of DNA that bind protein targets, such as oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al. 1994, *Mol Biol Rep* 20:97-107; Wallis et al. 1995, *Chem Biol* 2:543-552; Ellington 1994, *Curr Biol* 4:427-429; Lato et al. 1995, *Chem Biol* 2:291-303; Conrad et al. 1995, *Mol Divers* 1:69-78; and Uphoff et al. 1996, *Curr Opin Struct Biol* 6:281-287].

Certain RNA inhibiting agents may be utilized to inhibit the expression or translation of messenger RNA ("mRNA") that is associated with a phenotype of interest. Examples of such agents suitable for use herein include, but are not limited to, short interfering RNA ("siRNA"), ribozymes, aptamers, and antisense oligonucleotides.

In some instances, a range of 18-25 nucleotides is the most preferred size for siRNAs. siRNAs can also include short hairpin RNAs in which both strands of an siRNA duplex are included within a single RNA molecule. siRNA includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides. Such alterations can include the addition of non-nucleotide material, such as to the end(s) of the RNA or internally (at one or more nucleotides of the RNA).

In one embodiment, the RNA molecules contain a 3' hydroxyl group. Nucleotides in the RNA molecules of the present invention can also comprise non-standard nucleotides, including non-naturally occurring nucleotides or deoxyribonucleotides. Collectively, all such altered RNAs are referred to as analogues of RNA. siRNAs of the present invention need only be sufficiently similar to natural RNA that it, has the ability to mediate RNA interference (RNAi).

Methods for designing double stranded RNA to inhibit gene expression in a target cell are known (see, e.g., U.S. Pat. No. 6,506,559; Elbashir et al. 2002, *Methods* 26:199-213; Chalk et al. 2004, *Biochem Biophys Res Commun* 319:264-274; Cui et al. 2004, *Comput Methods Programs Biomed* 75:67-73; Wang et al. 2004, *Bioinformatics* 20:1818-1820). For example, design of siRNAs (including hairpins) typically follow known thermodynamic rules (see, e.g., Schwarz, et al. 2003, *Cell* 115:199-208; Reynolds et al. 2004, *Nat Biotechnol.* 22:326-330; Khvorova et al. 2003, *Cell* 115:209-216). Many computer programs are available for selecting regions of a sequence that are suitable target sites. These include programs available through commercial sources such as Ambion, Dharmacon, Promega, Invitrogen, Ziagen, and GenScript as well as non-commercial sources such as EMBOSS, The Wistar Institute, Whitehead Institute, and others.

For example, design can be based on the following considerations. Typically, shorter sequences, less than about 30 nucleotides are selected. The coding region of the mRNA is usually targeted. The search for an appropriate target sequence optionally begins 50-100 nucleotides downstream of the start codon, as untranslated region binding proteins and/or translation initiation complexes may interfere with the binding of the siRNA endonuclease complex. Some algorithms, e.g., based on the work of Elbashir et al. 2000 (*Methods* 26:199-213) search for a selected sequence motif and select hits, with approximately 50% G/C-content (30% to 70% has also worked). If no suitable sequences are found, the search is extended.

Other nucleic acids, e.g., ribozymes, antisense, can also be designed based on known principles. For example, Sfold (see, e.g., Ding, et al., *Nucl Acids Res* 32 Web Server issue, W135-W141; Ding & Lawrence 2003, *Nucl Acids Res* 31:7280-7301; and Ding & Lawrence 2001, *Nucl Acids Res* 20:1034-1046) provides programs relating to designing ribozymes and antisense, as well as siRNAs.

In one embodiment, downregulation of the functional level of activin is achieved by administering follistatin, inhibin, an antibody directed to activin, an activin antisense oligonucleotide, a non-functional activin molecule which competitively inhibits binding to the activin receptor or a mutant or soluble activin receptor which inhibits normal activin signalling.

It should be understood that in the context of the upregulation of follistatin levels, follistatin may reduce graft dysfunction by inhibiting activin functionality or it may function independently to activin. Without limiting the present invention to any one theory or mode of action, follistatin is a blocker of other TGFβ members and can, independently of activin, reduce graft dysfunction.

The method of the present invention is predicated on the determination that treatment of graft tissue with an activin inhibitor or follistatin downregulates the onset or course of graft tissue dysfunction subsequently to its harvesting. In this regard, it should be understood that the subject graft may be contacted with said inhibitor or said follistatin by any suitable means including, but not limited to:
(i) administering said inhibitor or follistatin to the graft donor, prior to removal of the graft; or
(ii) administration of said inhibitor or follistatin directly to the graft tissue either before or subsequent to its removal from a donor but prior to its transplantation; This method will be of particular importance where the graft is derived from stored tissues or tissues which have been generated or cultured in vitro;
(iii) administration of said inhibitor follistatin to the graft or graft recipient at or about (such as prior to) the time of graft transplantation or after transplantation;
(iv) a combination of two or more of the above.

Preferably, the graft is treated in accordance with the method of the invention at the time of collection or prior to harvesting. To this end, other molecules may also be simultaneously or sequentially administered, such as immunosuppressive drugs (if the organ is immunocompetent, such as spleen), agents to assist in maintaining tissue viability, antibiotics or other anti-pathogenic agent or the like. The present invention therefore further contemplates a combination of treatments, such as the administration of the agent together with other proteinaceous or non-proteinaceous molecules which may facilitate the desired therapeutic or prophylactic outcome. In one particular example, said inhibitor or follistatin is added directly to the donor tissue preservation solution at the time of tissue collection. Alternatively, the inhibitor or follistatin may be infused into a donor who is on life support, prior to harvesting of the organs. The inhibitor or follistatin may be administered as a single dose or may be administered as multiple sequential doses or it may be continuously infused. Where more than one molecule is administered, there, may be simultaneous administration in the same formulation or in different formulations via the same or different routes or sequential administration via the same or different routes. By "sequential" administration is meant a time difference of from seconds, minutes, hours or days.

The pharmaceutical compositions of the invention can be administered in a variety of unit dosage forms depending upon the method of administration. Dosages for typical modulatory pharmaceutical compositions are well known to those of skill in the art. Such dosages are typically advisory in nature and are adjusted depending on the particular therapeutic context, patient or organ tolerance, etc. The amount of agent adequate to accomplish this is defined as a "therapeutically effective dose." The dosage schedule and amounts effective for this use, i.e., the "dosing regimen," will depend upon a variety of factors, including the condition of the organ/graft, the pre-existence or not of dysfunction onset, the type of organ, the pharmaceutical formulation and concentration of active agent, and the like. In calculating the dosage regimen for an organ, the mode of administration also is taken into consideration. The dosage regimen must also take into consideration the pharmacokinetics, i.e., the pharmaceutical composition's rate of absorption, bioavailability, metabolism, clearance, and the like. (See, e.g., the latest Remington's; Egleton and Davis 1997 *Peptides* 18:1431-1439; Langer 1990 *Science* 249:1527-1533).

Preferably the graft is treated with the activin inhibitor or follistatin prior to transplantation. In this regard, treatment of the graft in this manner is referred to as "pretreatment" such as adding said inhibitor or follistatin to the organ preservation medium which is used after an organ is harvested. The subject pretreatment may be achieved by any suitable means which would be well known to the person of skill in the art. It should be understood that the design of a suitable protocol for treating a graft would be a matter of routine procedure for the person of skill in the art. Issues to be considered would include the point in time at which treatment should commence and at which treatment should cease. To this end, issues such as the concentration of inhibitor or follistatin to be administered and the frequency and number of doses also requires consideration. To the extent that the method of treatment is discontinued, it may be necessary to reinstitute treatment if symptoms of dysfunction, such as an upregulation in inflammation, are observed to occur.

Accordingly, there is provided a method of downregulating the onset or progression of mammalian graft tissue dysfunction said method comprising pretreating said tissue with an effective amount of an inhibitor of activin for a time and under conditions sufficient to downregulate activin functionality.

In another embodiment there is provided a method of downregulating the onset or progression of mammalian graft tissue dysfunction said method comprising pretreating said tissue with an effective amount of follistatin.

Preferably, said graft is lung, heart, kidney or liver.

An "effective amount" means an amount necessary at least partly to attain the desired result, or to delay the onset or inhibit progression or halt altogether, the onset or progression of the dysfunction. The amount varies depending upon the health and physical condition of the organ to be treated, the type of organ to be treated, the taxonomic group of the organ to be treated, the degree of protection desired, the formulation of the composition, the assessment of the medical situation, and other relevant factors. It is expected that the amount will fall in a relatively broad range that can be determined through routine trials.

A further aspect of the present invention relates to the use of the invention in relation to the treatment and/or prophylaxis of conditions which are characterised by graft dysfunction. Although it is envisioned that grafts would be treated prior to the onset of dysfunction, it is envisioned that where grafts were not initially pretreated, they could be treated subsequently to the onset of dysfunction, for example in order to reduce its severity. Grafts can also be treated after transplantation. Alternatively, the recipient can be treated before or after receipt of the graft or the donor can be treated prior to organ harvesting. Again, if a graft has not been pretreated, or if a previous pretreatment program was discontinued, a graft may be treated after transplantation in order to reduce the possibility of dysfunction onset or to reduce the severity or extent of a dysfunction process which may already have commenced. Accordingly, the method of the invention has application both prophylactically and therapeutically.

Accordingly, another aspect of the present invention provides a method for the prophylactic and/or therapeutic treatment of a condition characterised by mammalian graft tissue dysfunction said method comprising downregulating the functional level of activin in said tissue.

In still another aspect of the present invention provides a method for the prophylactic and/or therapeutic treatment of a condition characterised by mammalian graft tissue dysfunction said method comprising upregulating the functional level of follistatin said tissue.

Preferably, said graft tissue is lung, heart, kidney or liver.

More preferably, said graft is pretreated with said inhibitor.

Reference herein to "therapeutic" and "prophylactic" treatment is to be considered in its broadest context. The term "therapeutic" does not necessarily imply that an organ is treated until total recovery. Similarly, "prophylactic" does not necessarily mean that the organ will not eventually undergo some degree of dysfunction. Accordingly, therapeutic and prophylactic treatment includes amelioration of the symptoms of dysfunction or preventing or otherwise reducing the risk of developing dysfunction. The term "prophylactic" may be considered as reducing the severity or the onset of dysfunction. "Therapeutic" may also reduce the severity of an existing dysfunction.

In yet another aspect there is provided the use of follistatin or an inhibitor of activin in the manufacture of a medicament for the treatment of mammalian graft tissue dysfunction.

Yet another aspect of the invention is directed to an inhibitor of activin functionality for use in the therapeutic or prophylactic treatment of graft tissue dysfunction.

Still another aspect of the present invention is directed to follistatin for use in the therapeutic or prophylactic treatment of graft tissue dysfunction.

Preferably, said graft is lung, heart, kidney or liver.

Yet more preferably, said graft is pretreated with said inhibitor or follistatin.

The present invention is further described by reference to the following non-limiting examples.

Example 1—Lung Transplantation

Study Details

This study was approved by the Human Research and Ethics Committee, Alfred Hospital, and adhered to the principle of the Declaration of Helsinki. Patients were recruited from those being treated at the Department of Allergy, Immunology and Respiratory Medicine and that were to undergo a bilateral lung transplant as part of their clinical management. Patients were consented for this study and were of three cohorts based on the underlying requirement for a lung transplant. Group 1, obstructive CF, were those patients who had some airflow obstruction that may or may not be reversible, such that FEV 1 (Forced Expiratory Volume in 1 second) was decreased, as was the forced expiratory ratio (FER). Group 2, restrictive, related to increased FER with low lung volumes typical of idiopathic pulmonary fibrosis (IPF) patients. Group 3, obstructive, non-CF, related to those with severe emphysema, such as in chronic obstructive pulmonary disease (COPD), or severe asthma. A total of 55 patients with these underlying conditions were consented for this study, with subsequent ineligibility arising from those that had a single lung transplant (as opposed to bilateral), those who required extra-corporeal membrane oxygenation (ECMO) or were put on cardio-pulmonary bypass during the transplantation procedure. After exclusions, 11 patients in Group 1 were analysed (obstructive CF), along with 10 patients in Group 2 (restrictive) and 27 patients in Group 3 (obstructive non-CF).

Patients in this study were stratified into those that received lung transplants from a clinically dead donor (DCD) or non-clinically dead (non-DCD). They were further randomised to investigate the value of ischemic pre-conditioning. This modality is a recently utilised procedure that aims to protect the heart following major surgical insults, by providing brief episodes of non-lethal ischemia and reperfusion (Hausenloy & Yellon 2011, *Nat Rev Cardiol* 8:619-629). In the current protocol, patients were randomised to receive either ischemic pre-conditioning or the usual care protocol for this transplant procedure (no ischemic pre-conditioning). The pre-conditioning protocol involved a tourniquet being placed on the left leg at mid-thigh level after the induction of anesthesia. If the patient had been randomised to the usual care arm, the tourniquet was left deflated during the entire surgical procedure. If randomised to the ischemic pre-conditioning arm, at ~45 minutes before the planned reperfusion of the first transplanted lung the thigh tourniquet was inflated for five minutes, followed by five minutes of deflation. This inflation and deflation cycle was repeated another two times, resulting in 30 minutes of ischemia pre-conditioning with three cycles of inflation and deflation of the tourniquet.

In addition to the above procedure, blood samples were collected after the induction of anesthesia at the commencement of the transplantation procedure, at 15 minutes before the time of first lung reperfusion (15 minutes after the completion of the ischemia pre-conditioning, if performed), 15 minutes after reperfusion of the first lung, and two hours after reperfusion. After transfer of the patient to the intensive care unit (ICU), further blood samples were obtained eight and 24 hours post-reperfusion. Blood samples were centrifuged and plasma stored at −20 C until cytokine and chemokines were analysed.

The numbers of patients in each study group, following randomisation to ischemia pre-conditioning, transplantation of DCD or non-DCD lungs, after exclusions, are given in Table 1.

Immunoassay Analysis

Plasma samples were analysed for concentrations of a number of cytokines and chemokines. Concentrations of activin A were determined using a two-site ELISA (Oxford Bio-innovations, Cherwell, Oxfordshire, UK) as previously published (Knight et al. 1996, *J Endocrinol* 148:267-279). This assay measures both free and follistatin-bound activin A dimers and has no significant cross-reaction with other activin isoforms, such as activin B. Follistatin concentrations were determined using an extensively validated radioimmunoassay (O'Connor et al. 1999, *Hum Reprod* 14:827-832). In addition, CXCL8/IL-8, CCL5/RANTES, CXCL9/MIG, CCL2/MCP-1, CXCL 10/IP-10, interleukin (IL)-2, IL-4, IL-6, IL-10, tumour necrosis factor-$\alpha$ (TNF-$\alpha$) and interferon-$\gamma$ (IFN-$\gamma$) were determined using cytobead arrays (Becton-Dickinson).

Statistical Analyses

Regarding activin A and follistatin, an index of activin bioavailability was derived by calculating the activin/follistatin ratio. Furthermore, activin A and follistatin concentrations in the transplant patients were compared to the normal ranges for these proteins generated using healthy adult volunteers (D. J. Phillips & D. M. de Kretser, unpublished observations). Comparisons between baseline concentrations in transplant patients and normal range values were made using Student's t-test, or the Mann-Whitney test for non-parametric distributions. Correlation analyses were carried out using Pearson correlations for parametric data or Spearman correlations for non-parametric distributions. This was performed on all samples collected during lung transplantation (including baseline of those eligible patients) or only on the baseline sample from all consented patients.

Results

Basal, concentrations of activin A were elevated in patients undergoing transplantation in all three groups, when compared with normal ranges in healthy adults (Table 2). However, baseline follistatin concentrations in transplant patients were not different when compared with healthy adults, although there was some variability in concentrations beyond the normal range, as shown by the 95% confidence limits.

In general, there was no effect whether the transplant patient received lung transplants from DCD donors or not, or underwent ischemic pre-conditioning or the usual care protocol. This was assessed in terms of activin A and follistatin profiles, peak concentration and fold response (data not shown). Nevertheless, there was a trend for conditioning to lead to, slightly lower concentrations of both activin A and follistatin during and following lung transplantation (FIG. 1).

Figure 2:
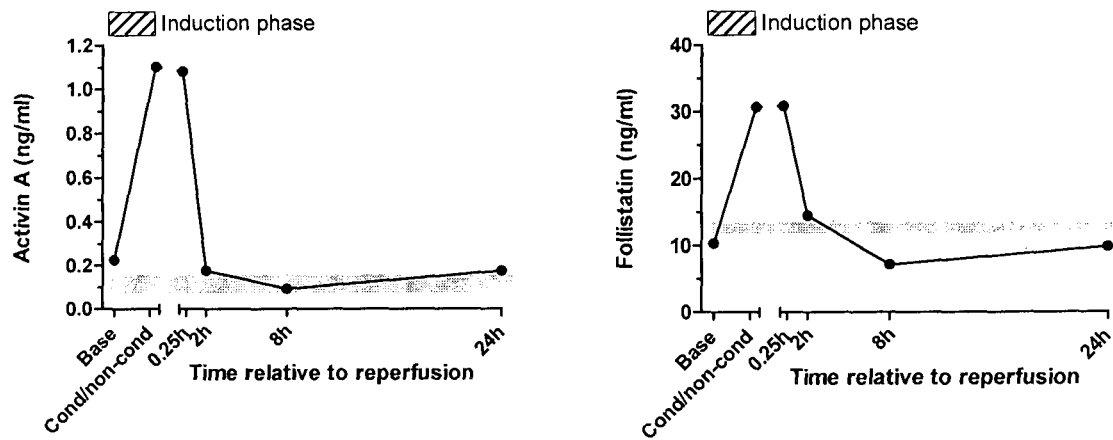
FIG. 2: Plasma concentrations of activin A (left panel) and follistatin (right panel) in a lung transplant patient, R45. The shaded bar in each panel indicates the normal range for both activin A and follistatin, and the hatched box indicates the period of surgery/reperfusion during the transplantation procedure.

There was a notable increase in both activin A and follistatin concentrations in transplant patients, such that peak concentrations were noted in most patients at the sample taken ~15 minutes before transplant reperfusion. The mean response to lung transplantation surgery was ~5-fold and ~2.5-fold basal concentrations for activin A and follistatin, respectively. This response varied between patients, with some having up to ~16-fold and ~5-fold changes, respectively. This response was independent of the status of the donor lungs or conditioning and is consistent with an induction response to major surgical trauma. An individual patient profile representative of this response in activin A and follistatin concentrations is depicted in FIG. 2.

Correlation analyses were performed between the various cytokines and chemokines measured in transplant patient samples. Activin and follistatin were significantly correlated with each other ($r=0.80$, $p<0.0001$). The activin/follistatin ratio, an index of activin bioavailability was also significantly correlated with each protein (activin: $r=0.87$, $p<0.0001$, follistatin: $r=0.54$). Of the other cytokines and chemokines, significant positive correlations of both activin A and follistatin were noted with CCL5/RANTES (activin: $r=0.35$, $p<0.0001$, follistatin: $r=0.29$, $p<0.0001$), CXCL9/MIG (activin: $r=0.51$, $p<0.0001$, follistatin: $r=0.51$, $p<0.0001$) and CXCL10/IP-10 (activin: $r=0.32$, $p<0.0001$, follistatin: $r=0.34$, $p<0.0001$). Other correlations with cytokines and chemokines were not statistically significant. However, when baseline concentrations of activin A and follistatin were compared with the cytokines and chemokines measured, activin A baseline concentrations were correlated with IL-8 ($r=0.29$, $p<0.05$) and CXCL9/MIG ($r=0.46$, $p<0.001$) and follistatin baseline concentrations were correlated with CCL5/RANTES ($r=0.27$, $p<0.05$) and CXCL9/MIG ($r=0.27$, $p<0.05$). Of interest was that the activin/follistatin ratio in baseline samples was correlated with IL-8 ($r=0.35$, $p<0.05$), CXCL9/MIG ($r=0.38$, $p<0.01$), CCL2/MCP-1 ($r=0.27$, $p<0.05$), CXCL10/IP-10 ($r=0.33$, $p<0.05$), TNF-α ($r=0.27$, $p<0.05$) and IFN-γ ($r=0.44$, $p<0.01$).

Example 2—Long Term Follow Up of Lung Transplantation Patients

Viral infections are common following lung transplantation, with 50% of recipients demonstrating cytomegalovirus (CMV) reactivation in the allograft or blood as well as a further 60% acquiring a respiratory RNA viral infection. As viral infections are postulated to trigger the development of acute rejection and (BOS) the serum activin A, activin B and follistatin levels are measured during and following CMV reactivation and infection. Further acute rejection episodes of grade A1 occur in 25% of patients and grade A2 or greater in 10% in the first 3 months post-transplant. Clinical criteria available include lung function (FEV 1, % best achieved), acute cellular rejection, ICU data, infection (bacterial/fungal/viral), immunosuppression and survival. New patients undergoing lung transplantation have blood collected prior to anesthesia, immediately prior to reperfusion of the lung and at 2, 8 and 24, 48 and 72 hours later, and daily for the first week post-transplantation for measurements of circulating activin A, B and follistatin during the period when primary graft disfunction may occur and the patients followed as described earlier.

Example 3—Pig Renal Transplants

Fourteen immature pigs were tranquilized with an intramuscular injection of xylazine and tiletamine/zolazepam, intubated and maintained on mechanical ventilation of 1% isoflurane in a 50% oxygen mixture. Electrocardiogram, oxygen saturation and rectal temperature was monitored throughout the procedure. An external jugular vein was exposed and a single-lumen catheter was inserted, with tunneling of the catheter through the skin to allow blood samples to be collected at various times throughout and following the transplantation surgery. Thereafter, a midline laparotomy was performed, followed by exposure of the right kidney. A right nephrectomy was performed, followed by dividing the renal artery and vein in the hilum to allow anastomosing of a donor kidney. During post-operative recovery, the animal had free access to food and water. Serum derived from the blood samples collected were analysed for activin A and follistatin concentrations using well-validated immunoassays (Knight et al. 1996 supra; O'Connor et al. 1999 supra).

Results

Using a sensitive ELISA to measure serum activin and an a radioimmunoassay to measure follistatin the data demonstrate that these levels are markedly elevated in the induction phase and reperfusion phases in pigs under going renal transplantation similar to the data in human lung transplantation (Table 3).

Example 4—Human Liver Transplantation

Serum activin and follistatin response to liver transplantation surgery demonstrated similar patterns to that observed in patients undergoing lung transplantation (Table 4).

Example 5—Use of Non-Heparin Anti-Coagulants in Organ Retrieval and Transplant Engraftment Normally during lung transplantation procedures, a donor receives 25,000 units of unfractionated heparin just before clamping the pulmonary artery and the recipient receives 5000 units at the induction of anesthesia and before clamping each pulmonary artery. The impact of anticoagulant use on donor organ activin A levels is assessed.

Adult male Sprague Dawley rats (n=7 rats per group) are anesthetised using ketamine and xylazine. Through a catheter in the right atrium introduced via the internal jugular vein, a basal blood sample is taken and 250 units/kg body weight of unfractionated heparin given to one group, and an equivalent anti-coagulant dose of lepirudin or saline of equivalent volume to the other groups. Blood samples are collected at 30 and 60 minutes before sacrificing rats and the lungs, heart, kidneys and liver are removed and homogenised. Activin A, activin B and follistatin are measured in these extracts by established methods (Knight et al. 1996 supra; O'Connor et al. 1999 supra; Ludlow et al. 2009, *Clin Endocrinol*, 71:867-873). Further, normally the current treatment of the donor organs is that the pulmonary artery supplying the lung in the heparinised donor is clamped, the lung perfused with a preservation solution (Perfadex®) for 2-3 minutes and then bagged, immersed in Perfadex® and stored on ice for 4-12 hours. To model this scenario, rat lungs that are anticoagulated with either heparin or lepirudin are used, then flushed with Perfadex® with or without heparin or lepirudin over 2-3 minutes, as in the donor, and bagged and stored on ice for 6 hours. The lungs are then flushed with Perfadex® and the eluate collected to measure activin A, activin B and follistatin. The lungs are homogenised and the extracts used to determine the tissue content of the activin A, activin B and follistatin.

From donation after brain death (DBD) procedures, samples of blood (basal) are taken before and at 15 minutes after the 25,000 units of heparin are administered as routine preparation for organ donation. The preservation fluid used to flush the vasculature is collected to measure the activin A, activin B and follistatin released by heparin. These results are compared with DBDs given lepirudin, instead of heparin, as the anti-coagulant to identify anticoagulants which minimise activin A increase in the donor organ. They also provide a means of screening anticoagulants to identify preferred anticoagulants.

Figure 3:
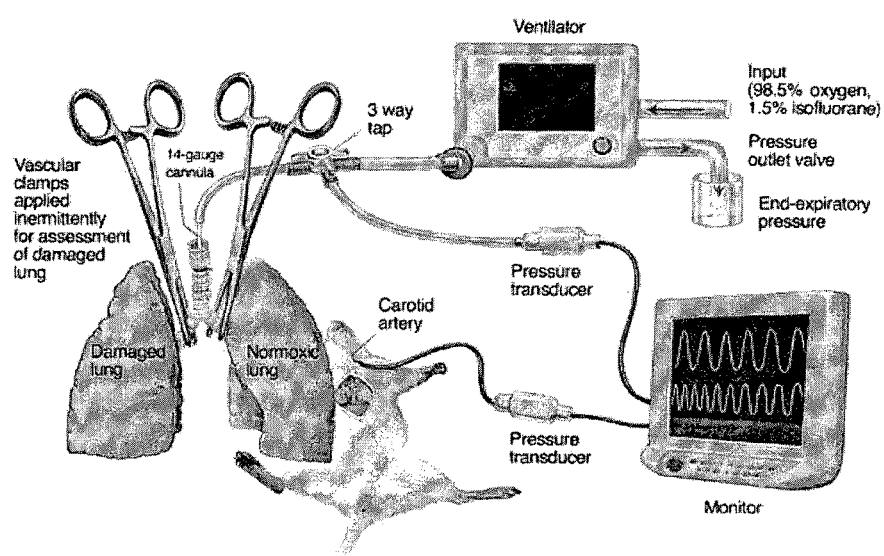
FIG. 3: Lung injury preparation in a rat model (from Lim et al. 2010, *ANZ J Surgery*, 80:265-270).

Example 6—Treatment of the Graft with Follistatin Before Engraftment to Decrease Graft Dysfuntion and Fibrosis Using a rat lung auto-transplantation model (Lim et al. 2010, ANZ J Surg, 80:265-270), groups of pathogen-free male Sprague Dawley rats are anesthetised using ketamine and xylazine and maintained on a mechanical ventilator using 1.5% isofluorane and 98.5% oxygen via a 14-gauge intratracheal intravenous catheter inserted via a tracheotomy. Arterial blood pressure and systemic oxygenation is monitored via a carotid artery catheter (FIG. 3).

After median sternotomy, one lung is maintained on normal oxygenation. The other is rendered ischemic using a non-crushing vascular clamp applied across the right bronchus and pulmonary vascular pedicle for 60 minutes and then removed to allow reperfusion. Before clamping, gas exchange function and pulmonary artery pressures are measured and repeated 30 and 60 minutes after lung reperfusion. Blood samples are taken immediately after induction of anesthesia, just prior to clamping the vascular pedicle and 90 minutes later just prior to vascular clamp removal. Further samples are drawn at the commencement of reperfusion and 60 and 120 minutes and the rats are killed and blood collected by cardiac puncture. This group receives the vehicle via the intra-carotid catheter at the time of induction of anesthesia.

Separate groups of rats are treated as follows. One group receives 30 µg human recombinant follistatin (hrFS), via the carotid catheter at the induction of anesthesia, simulating giving follistatin to both the donor and recipient. A second group receives the same dose given just prior to reperfusion, simulating giving follistatin to the recipient alone. The third group is given 30 µg hrFS into the pulmonary artery of the clamped lung, simulating adding follistatin to the lung preservation fluid (pneumoplegia). In three additional groups of rats, one for each of the above follistatin treatment programs, the surgical procedure is performed using aseptic techniques, chest closed and the rats allowed to recover for 4 days before being euthanased and their tissues taken for analysis of the parameters listed below. Serum levels of activin A, activin B and follistatin (Knight et al. 1996 supra; O'Connor 1999 supra; Ludlow et al. 2009 supra) and the inflammatory cytokines and chemokines (including IL-1β, IL6, IL12 p40, IL12 p70, IL17, G-CSF, GM-CSF, MCP1, MIP1α, MIP1β and TNFα) are assayed. Oxidative stress in the lung is assessed by measuring lipid hydroperoxides (DROMS) in the pulmonary effluent. The free radical analytical system (FRAS; Diacron International) is used to measure total oxidation products and antioxidant potential in blood, including long-lived hydroperoxides generated when lipids and proteins are damaged by ROS. The lungs are fixed by intra-tracheal instillation of 20% buffered formalin at constant pressure, post-fixed for a further 24 hours and embedded in paraffin. Quantitative cytological data is obtained by image analysis of sections stained using haematoxylin and eosin and the lung injury quantified from oedema, alveolar volumes, thickening of alveolar capillary membranes; bleeding and volume occupied by inflammatory infiltrate or degenerating cells. Activin βA, βB, FS288 and FS315 mRNA expression is measured in lung extracts by quantitative RT-PCR (QRT-PCR) and by ELISA and RIA. Their localisation in lung tissue is undertaken by immunohistochemistry, using established techniques Example 7—Regulation and Actions of Activin a and Follistatin in Myocardial Ischemia-Reperfusion Injury Materials and Methods
Reagents Bovine follistatin was purified from ovarian follicular fluid, as previously described (Robertson et al. 1987, Biochem Biophys Res Commun 149:744-749). Human recombinant activin A (R&D systems, Minneapolis, Minn., USA) was a generous gift from Dr. Craig Harrison (Prince. Henry's Institute, Victoria, Australia).

Experimental Animals

All animals were maintained in accordance with guidelines published by the National Institutes of Health and the Australian National Health and Medical Research Council. Experiments were approved by the Animal Ethics Committees of the University of Washington, Monash University and the Baker IDI.

In Situ Murine IR Model

Wild-type C57BL/6J and C57BL/10ScNJ TLR4$^{-/-}$ mice (The Jackson Laboratory, Bar Harbor, Me., USA) between 10-14 weeks old, 22-26 g, were subjected to 30 minutes ischemia followed by 120 minutes of reperfusion, as described previously (Chong et al. 2004, J Thorac Cardiovasc Surg 128:170-179.). Briefly, mice were anesthetised with intraperitoneal pentobarbital sodium (100 µg/g, Abbott Laboratories, North Chicago, Ill., USA), intubated and ventilated. A left parasternotomy was performed under a dissecting microscope (Zeiss, Oberkochen, Germany). A 7/0 silk suture (Tyco Health Care, Norwal, Conn., USA) was passed behind the left anterior descending artery (LAD), just distal to the left atrial appendage. The threads were then passed through the tip of a 22-gauge angiocatheter. The sutures could then be tightened and released by applying a clip at the end of the angiocatheter to restrict and restore blood flow. Sham mice underwent the same surgical procedures except the sutures were not tightened. In the treatment group, mice were injected intraperitoneally with 10 µg bovine follistatin, diluted in 1 ml of 0.9% saline just after anesthesia. Control mice received 1 ml of 0.9% saline alone.

Determination of Area at Risk (AAR) and Infarct Size

AAR and infarct area in the left ventricle of the mice were determined, as previously described (Chong et al. 2004, supra). The LAD was re-occluded at the end of the experimental protocol and 4% Evans blue dye (Sigma Aldrich, St. Louis, Mo., USA) was injected into the aortic root so that the LAD territory, which was the AAR, remained unstained as a result of the re-occlusion. Hearts were then removed, rinsed in 0.9% saline and embedded in 1% agarose gel (Invitrogen, Carlsbad, Calif., USA) in phosphate-buffered saline and sliced into 1 mm thick sections parallel to the short axis of the left ventricle and incubated in 1% triphenyltetrazolium chloride (Sigma Aldrich) at 37° C. for 20 minutes and 10% formalin (Sigma Aldrich) for 24 hours. The slices were then weighed and photographed using a digital camera. AAR and infarct area (area not stained by triphenyltetrazolium chloride) were measured by using computer planimetry (ImageJ 1.21 software; National Institutes of Health, USA).

Activin A ELISA

The activin A homodimer was measured by ELISA, as previously described (Knight et al. 1996, supra). The assay uses a sandwich design employing a monoclonal antibody (E4) raised against a synthetic peptide corresponding to residues 82-114 of the mature activin βA subunit and has been validated for both mouse serum and culture media (Knight et al. 1996, supra). The mean sensitivity was 13 pg/ml. The mean intra- and inter-assay coefficients of variation (CV) of the assay were 6.9% and 9% respectively.

Follistatin Radioimmunoassay (RIA)

Follistatin was measured by RIA as previously described (Klein et al. 1991, *Endocrinology*, 128:1048-1056). The assay employs purified heterologous bovine follistatin as standard and uses iodinated recombinant human follistatin as tracer. The assay sensitivity was 2.7 ng/ml, and the intra- and inter-assay CV values were 6.4 and 10.2%, respectively.

Quantitative Reverse Transcriptase-PCR (QRT-PCR)

The expression of Inhba, the gene expressing the βA subunit of activin A, and Fst, the follistatin gene, were measured by QRT-PCR, as described previously (Winnall et al. 2009 *Mol Cell Endocrinol*, 307:169-175). Total RNA was extracted from the left ventricular portion of the hearts using Trizol (Invitrogen) according to the manufacturer's instructions. Genomic DNA was removed using a DNAfree kit (Ambion, Austin, Tex., USA). cDNA was synthesized using the Superscript kit (Invitrogen). QRT-PCR was performed using a Biorad iQ5 system (BioRad, Hercules, Calif., USA) with FastStart DNA Master SYBR-green system (Roche, Basel, Switzerland). Data were analyzed using relative quantification, normalized against 18S mRNA as the house keeping gene and presented as fold change compared with control samples. Primers for mouse 18S mRNA were 5'-ACCGCAGCTAGGAATAATGGAA-3' (forward) and 5'-TCGGAACTACGACGGTATCTGA-3' (reverse); for Inhba (activin A) were 5'-TGGAGTGTGATGGCAAGGTC-3' (forward) and 5'-AGCCA CACTCCTCCAC AATC-3' (reverse) and for Fst (follistatin) 5'-CCACTTGTGTGGTG-GATCAG-3' (forward) and 5'-AGCTTCCTTCATGGCA-CACT-3' (reverse).

Mouse Neonatal Ventricular Cardiomyocyte (NVCM) Isolation and Culture

NVCM was isolated using a well established technique (Venardos et al. 2009, *J Cell Biochem* 108:156-168). Briefly, neonatal (1-2 day old) C57BL/6J mice were killed by decapitation and the ventricles dissected and exposed to trypsin (Gibco Laboratories, Grand Island, N.Y., USA) treatment overnight at 4° C. Cardiomyocytes were dissociated by serial collagenase ((Worthington Biochemical Corp., Freehold, N.J., USA) digestion at 37° C. Cells were then cultured in Dulbecco's modified Eagle's media (Gibco Laboratories) supplemented with 10% foetal bovine serum and antibiotics (Invitrogen, Carlsbad, Calif., USA). Cultures were serum-starved for 24 hours, prior to experiment. The NVCM cultures were subject to 3 hours of hypoxia in a humidified 95% $N_2$/5% $CO_2$ flushed hypoxic chamber incubated at 37° C., followed by 2 hours of reoxygenation at 37° C. in 5% $CO_2$/air, as previously described (Venardos et al., 2009, supra). Normoxic control cells were incubated at 37° C. in 5% $CO_2$/air only. Recombinant activin A (50 ng/ml) or follistatin (100 ng/ml) were added to cardiomyocyte cultures just before experimentation under normoxic and hypoxia-reoxygenation (HR) conditions. Culture media were collected at the end and stored at −20° C. prior to assay.

Measurement of Lactate Dehydrogenase (LDH)

Release of LDH as a marker of cellular necrosis was measured in media collected from NVCMs, as previously described (Venardos et al., 2009, supra). Briefly, 1001 of 1 mmol/L NADH (Sigma Aldrich) was added to 800 ml of assay mix containing 125 mmol/L NaH2PO4 (pH 7.5) and 1.25 mmol/L sodium pyruvate (Sigma Aldrich). The LDH present in the samples reduces pyruvate to lactate using NADH as the electron donor. In the process NADH is oxidized to $NAD^+$ and no longer absorbs light. LDH activity was assessed spectrophotometrically by measuring the rate of decrease in absorbance at 340 nm over 2 min.

Measurement of Reactive Oxygen Species (ROS) Production

ROS production was measured as previously described (Venardos et al., 2009, supra). Briefly, ROS production was measured using the ROS sensitive flurochrome 2',7'-dichlorodihydro-fluorescein diacetate (H2DCF-DA, Invitrogen). Cardiomyocytes were incubated with phosphate-buffered saline supplemented with H2DCF-DA (10 μmol/L). Fluorescence measurements (excitation 485 nm, emission 520 nm) were expressed as relative fluorescence units/second (RFU/sec), with background fluorescence subtracted from the average of 8 readings.

Measurement of Mitochondrial Membrane Potential (MMP)

MMP was measured using the fluorescent probe 5,5',6,6'-tetrachloro-1,1,3,3'-tetraethylbenzimidazolylcarbocyanine iodide (JC-1, Molecular Probes, Invitrogen) according to the manufacturer's recommendations, as previously described (Winnall et al. 2009, supra). Inhibition of the electron transport chain promotes membrane depolarization which is detected by JC-1 probe via a decrease in red/green fluorescence intensity ratio. A minimum of S replicates were measured for each of these parameters and expressed as percentage change to the normoxic control group.

Statistical Analyses

The Graphpad Prism 5 graphical and statistics package (GraphPad Software Inc., San Diego, Calif., USA) was used for presentation and analysis of the data. Data are expressed as mean±standard error of the mean (SEM). Student's t-test and one way ANOVA were used to compare group data, as appropriate. Bonferroni's and Dunnett's post tests were used for multiple comparisons. A p value ≤0.05 was considered to be statistically significant.

Results

Myocardial Activin a Protein and mRNA Levels Following IR

Figure 4:
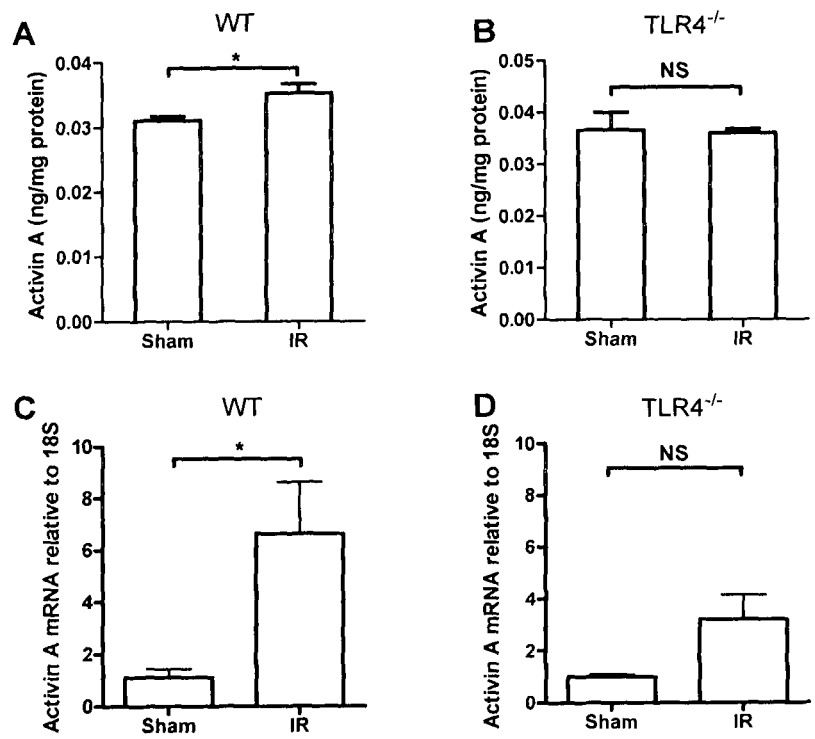
FIG. 4: Myocardial activin A levels in wild-type (WT) and TLR4$^{-/-}$ mice following ischemia-reperfusion (IR). Myocardial activin A protein levels in WT mice (A) and TLR4$^{-/-}$ mice (B) in IR and sham surgery groups measured by ELISA (N=5-6 mice in each group). Myocardial activin A mRNA levels in WT mice (C) and TLR4$^{-/-}$ mice (D) in IR and sham surgery groups measured by QRT-PCR. Activin A mRNA levels were normalized to 18S mRNA and expressed as fold increase over sham surgery group (N=3 mice in each group). Data are mean±SEM; * p<0.05; NS, non significant.

After 30 minutes of ischemia, using the in situ IR model, no changes were seen in myocardial or serum activin A protein levels between the ischemia and sham surgery groups (data not shown). However, myocardial activin A protein levels were increased by 16% and mRNA expression rose over 6-fold after a further 2 hours of reperfusion compared with the sham surgery group (p<0.05, FIG. 4A, 4C). In contrast to the wild-type mice, neither activin A protein nor mRNA levels were significantly up-regulated in $TLR4^{-/-}$ mice following IR (FIG. 4B, 4D).

Myocardial follistatin protein and mRNA levels following IR

Figure 5:
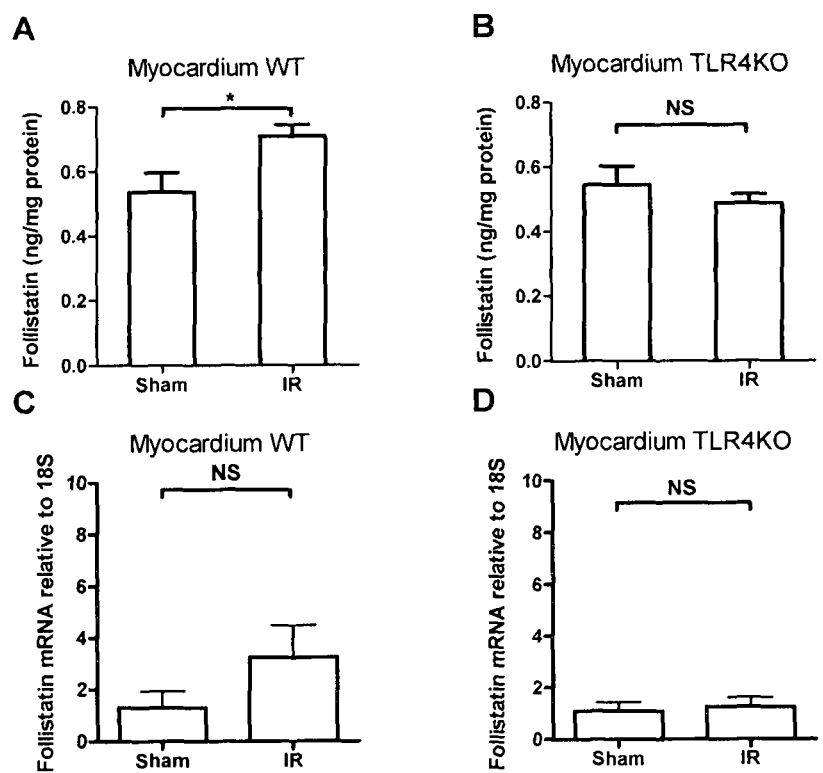
FIG. 5: Myocardial follistatin levels in wild type (WT) and TLR4$^{-/-}$ (TLR4KO) mice following ischemia-reperfusion (IR). Myocardial follistatin protein levels in WT mice (A) and TLR4$^{-/-}$ (TLR4KO) mice (B) in IR and sham surgery groups as measured by RIA (N=5-6 mice in each group). Myocardial follistatin mRNA levels in WT mice (C) and TLR4$^{-/-}$ (TLR4KO) mice (D) in IR and sham surgery groups measured by QRT-PCR. Follistatin mRNA levels were normalized to 18S mRNA and expressed as fold increase over sham surgery group (N=3-4 mice in each group). Data are mean SEM; * p<0.05; NS, non significant.

Myocardial follistatin levels did not change after 30 minutes of ischemia (data not shown). Myocardial follistatin protein levels increased by 31% after a further 2 hours of reperfusion. However, myocardial follistatin mRNA did not change significantly (FIG. 5A, 5C). There were no changes in follistatin protein or gene expression after IR in TLR4$^{-/-}$ mice (FIG. 5B, 5D).

Serum Activin a and Follistatin Levels Following IR

Figure 6:
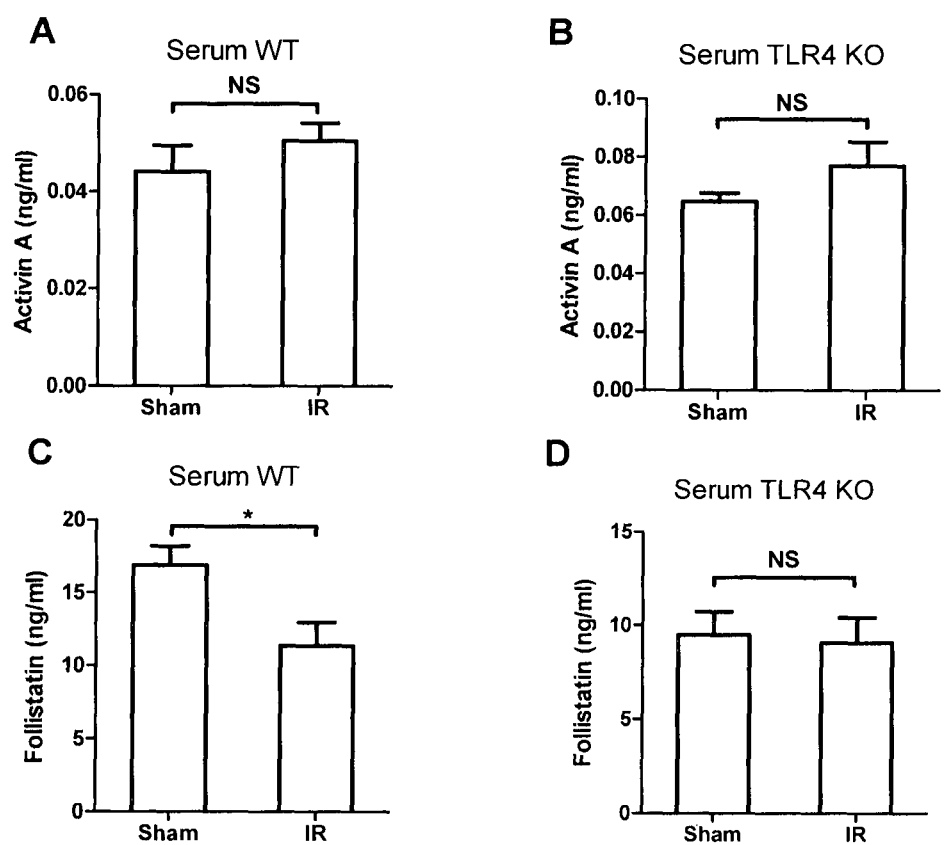
FIG. 6: Serum activin A and follistatin protein levels following ischemia reperfusion (IR). Serum activin A protein levels after IR in wild type (WT) mice (A) and TLR4$^{-/-}$ (TLR4KO) mice (B) measured by ELISA. Serum follistatin protein levels after IR in WT (C) and TLR4$^{-/-}$ (TLR4KO) mice (D) measured by RIA. N=5-6 mice in each group. Data are mean±SEM; * p<0.05; NS, non significant.

There was no significant change in serum activin A levels following 30 minutes of ischemia and 2 hours of reperfusion. However, a 33% reduction in serum follistatin levels was observed (FIG. 6A, 6C). In TLR4$^{-/-}$ mice, there were no changes in activin A and follistatin levels in serum following IR (FIG. 6B, 6D).

Effect of Follistatin Pretreatment on Cardiac IR Injury In Vivo

Figure 7:
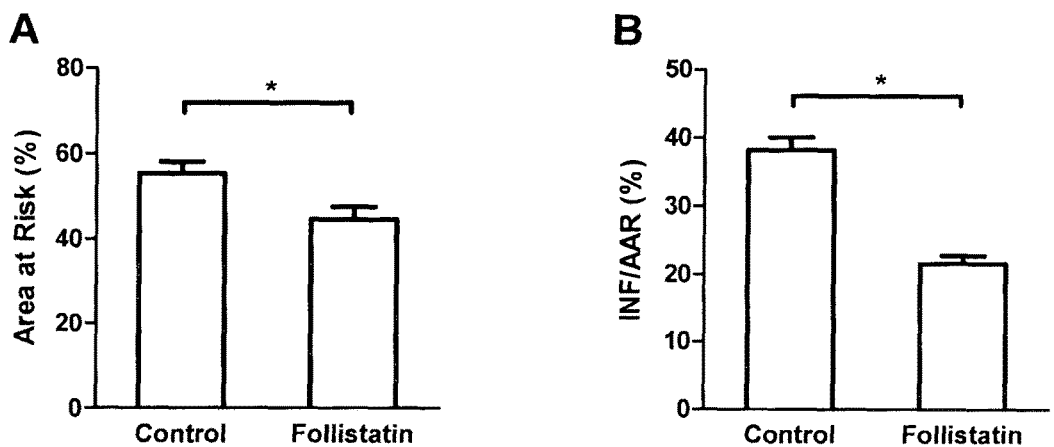
FIG. 7: Effect of follistatin pre-treatment on myocardial infarct size following ischemia-reperfusion. (A) Area at risk of myocardium defined by Evans blue dye in saline control and follistatin treated groups. (B) Infarct size as a ratio of the area at risk in saline control and follistatin treated groups (N=9 mice in each group). Data are mean±SEM; * p<0.05.

In order to examine whether inhibition of activin A action by blockade with follistatin can reduce myocardial IR injury, mice were pretreated with bovine follistatin and then subjected to in situ myocardial IR. Pretreatment with follistatin resulted in a significantly smaller (45% vs. 55%, p<0.05) myocardial AAR compared with the control group (FIG. 7A). However, the infarct area, expressed as a ratio of the AAR, was significantly smaller in the follistatin-treated group (22% vs. 38%, p<0.05; FIG. 7B).

Effect of Follistatin on Cardiomyocyte LDH Release In Vitro

Figure 8:
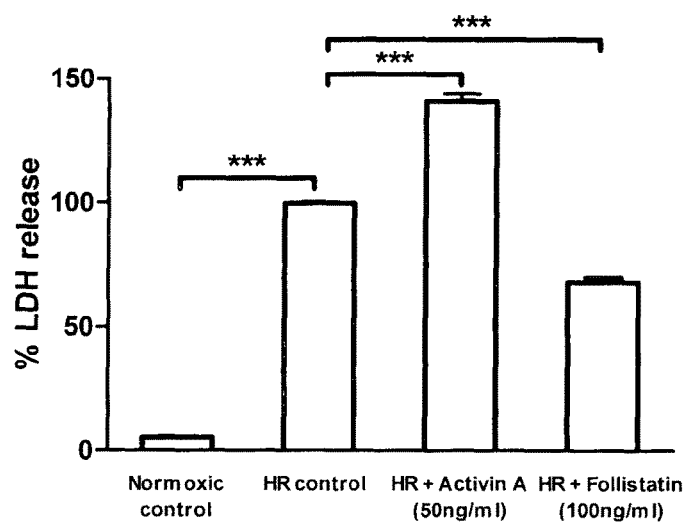
FIG. 8: Effect of activin A and follistatin co-treatment on LDH release from cultured mouse NVCM undergoing hypoxia re-oxygenation (HR) in vitro. LDH, a marker of cellular injury, was measured in the culture media in mouse neonatal cardiomyocyte culture in normoxic and hypoxia (3 hours) and re-oxygenation (2 hours) conditions with or without activin A or follistatin treatment. The level of LDH release from the HR group without any treatment was used as a reference group. Normoxic control and HR with the addition of either activin A or follistatin were expressed as percentage changes from the HR control. Data are mean±SEM. Experiments were done in triplicate in three separate experiments; ***p<0.001.

In order to confirm the protective effects of follistatin seen in vivo, mouse NVCM cultures undergoing HR in vitro were treated with activin A or follistatin, with LDH levels measured as a marker of cellular necrosis. Addition of activin A increased LDH levels by 41% (p<0.0001 vs. untreated HR control), whereas follistatin treatment resulted in a 32% (p<0.0001) reduction in LDH levels compared with untreated HR controls (FIG. 8). These data indicate that activin A increases cell death in NVCM subjected to HR in culture, while follistatin reduces the cell death.

Figure 9:
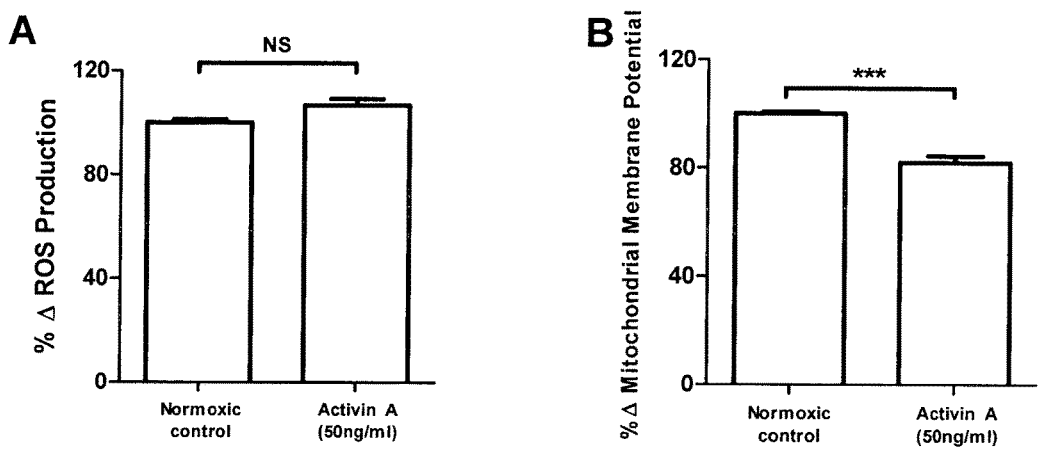
FIG. 9: ROS production and mitochondrial membrane potential in cultured mouse NVCM following activin A treatment under normoxic conditions. Changes in ROS production (A) and mitochondrial membrane potential (B) measured in 5 hour cultures under normoxic conditions with or without activin A co-treatment. Data are mean±SEM. Experiments were performed with 6 replicates (data shown) and the experiment was repeated twice with similar results; *** p<0.001; NS, non significant.
Figure 10:
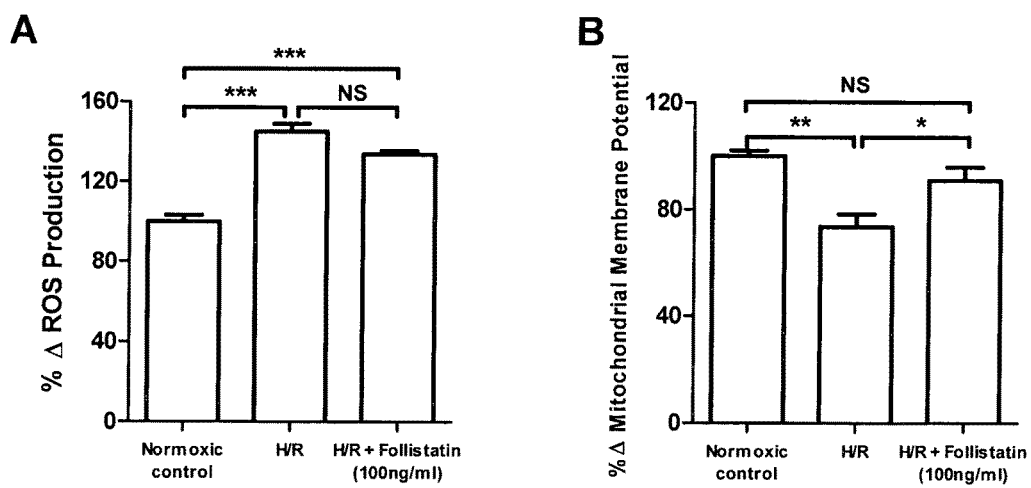
FIG. 10: ROS production and mitochondrial membrane potential in cultured mouse NVCM following follistatin treatment in hypoxia-reoxygenation (H/R) condition. Changes in ROS production (A) and mitochondrial membrane potential (B) measured following 3 hours of hypoxia and 2 hours of re-oxygenation with or without follistatin co-treatment. Data are mean±SEM. Experiments were done in 6 replicates and the experiment was repeated twice with similar results; * p<0.05,  p<0.01, *p<0.001; NS, non significant.

Effect of Activin and Follistatin Treatment on Cardiomyocyte ROS Production and MMP The effects of activin A and potential protective mechanisms of follistatin in IR/HR were investigated by measuring cardiomyocyte ROS production and MMP. Activin A treatment, under normoxic conditions, did not result in a significant change in cardiomyocyte ROS production, but significantly reduced the MMP of these cells (FIG. 9A-B). As expected, HR resulted in 45% increase in ROS production and reduced MMP to 74%. Follistatin treatment under HR conditions did not reduce ROS production but significantly restored MMP (74% to 91% of normoxic control; FIG. 10A-B)

Figure 11:
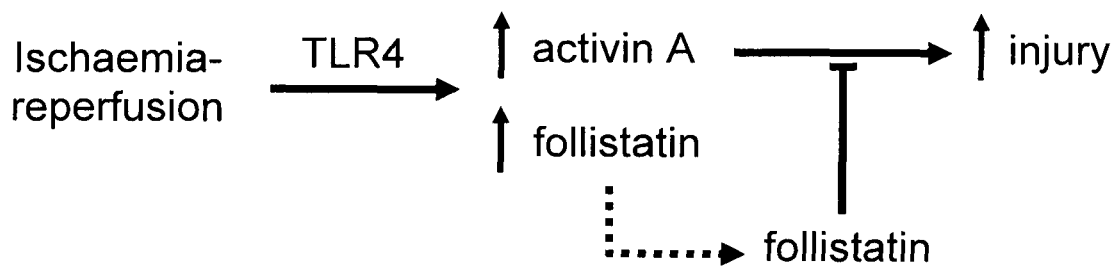
FIG. 11: Summary diagram: Ischemia-reperfusion, acting via a TLR4-mediated mechanism, stimulates expression of activin A and its binding protein, follistatin, in cardiomyocytes. Administration of follistatin reduces the injury to cardiomyocytes caused by ischemia-reperfusion or by hypoxia-reoxygenation in vitro. These data indicate that activin A is an intermediate in the pathway to cardiomyocyte damage, and that both endogenously-produced and exogenously-administered follistatin can act as a regulator of this pathway.

Altogether, these data suggest that IR, acting through TLR4, stimulates activin A expression in the myocardium, which is able to damage the cardiomyocytes. Blocking activin action by exogenous follistatin reduces the subsequent damage. However, the damage to cardiomyocytes caused by activin A appears to be independent of, and hence is not mediated by, increased ROS production. These data suggest a causative role for activin A in myocardial IR injury and that blocking activin effects with follistatin can be protective in this setting (FIG. 11).

Example 8—Administration of Follistatin to Attenuate Ischemia Reperfusion (IRI) Injury of the Kidney Design:

Mice were unilaterally nephrectomised and the remaining kidney underwent a period of ischemia by clamping the renal vascular pedicel for 20 mins. The clamp was then released and the mice allowed to recover for 24 hrs following which they were killed. Some adult mice were killed before any experimentation and blood and kidney tissue collected were termed "Basal". All other mice were anesthetised and in one group, termed "sham", the kidneys were exposed and then the abdomen was closed and blood and kidney samples collected. In all other mice, a unilateral nephrectomy was performed such that the mice were surviving on one kidney only. In these unilaterally nephrectomised mice, the remaining kidney was subjected to a period of ischemia of 20 minutes by clamping the renal blood vessels and then reperfusion to create an ischemic-reperfusion injury (IRI). The mice were allowed to survive for 24 hours after which they were killed by exsanguination to collect blood and their kidneys were assessed to determine the severity of the renal damage. The latter was also assessed by the measurement of serum creatinine. Using this model, groups of mice were given either follistatin-288 (FS), 5 μg in saline, or saline (vehicle) by intraperitoneal injection either 30 or 60 minutes before the IRI. The activin A, activin B and follistatin levels were measured in the blood samples from all groups.

Methods:

8-10 week old C57BL/6 mice are anesthetised; midline incision to expose both kidneys. The left kidney is removed and microvascular clamp applied to the right renal pedicle for 20 mins. During this time the mice are kept at 37° C. (monitored via rectal probe). After this time the clamp is removed and blood allowed to return to the kidney. Midline incision is sutured and mice are allowed to recover. The administration of 5 μg follistatin (IP) was performed 30 or 60 mins prior to IRI induction.

Tubular injury score: after 24 of reperfusion the mice are euthanased and kidney retrieved and paraffin embedded. 4 μm slices are stained with H&E. The tubular injury score is determined by assessing the degree of tubular injury in the upper, mid and lower poles of the kidney. A score is assigned according to the extent of injury within the renal cortex. Eg: 0=0%; 1=1-25%; 2=26-50%; 3=51-75%; 4>75%. The sections are assessed blindly by a nephrologist and renal histopathologist.

Serum creatinine levels: Serum creatinine levels were measured using a serum creatinine kit supplied by Abcam according to manufacturers instructions.

Statistical analysis: comparisons between different treatments were conducted using Mann-Whitney test for non-parametric distributions.

Figure 12:
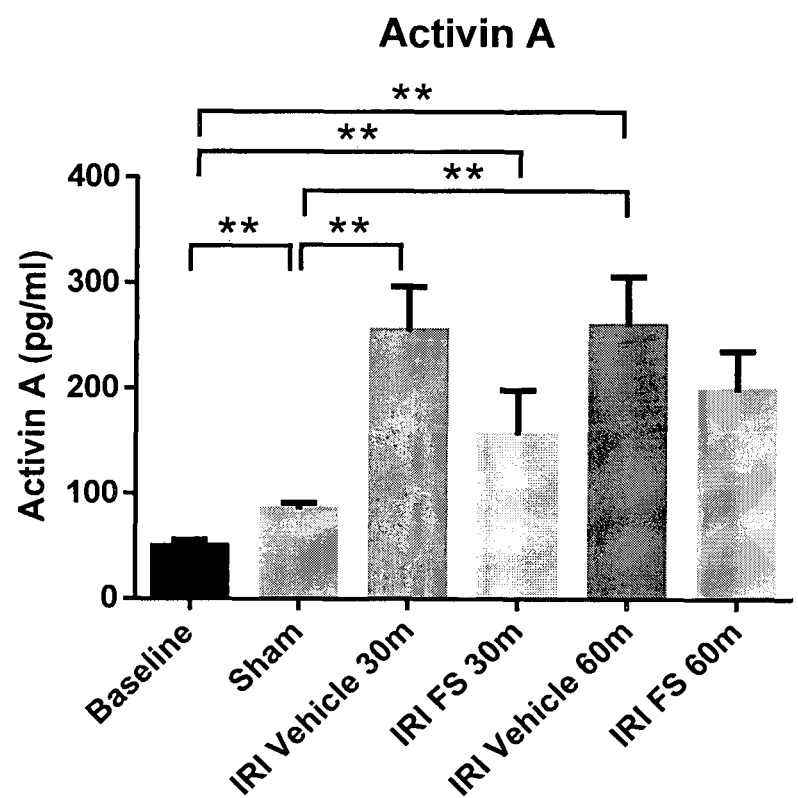
FIG. 12: Serum activin A protein levels following renal ischemia-reperfusion injury (IRI) in mouse. Serum activin A protein levels in baseline, sham and IRI groups 24 hrs after IRI as measured by ELISA. Mice in IRI groups were further divided into treatment groups receiving IP administration of either vehicle or follistatin (FS, 5 μg/mouse) 30 mins (30 m) or 60 mins (60 m) prior to IRI. Note the significant increase in activin A levels between basal and sham groups, consistent with the response to surgical stress. Also note the further significant increases induced by IRI in the vehicle treated groups and the lower levels of activin A in the mice given follistatin 30 and 60 minutes before the IRI. Data are mean±SEM; N=4-6 mice per group; **p<0.01.
Figure 13:
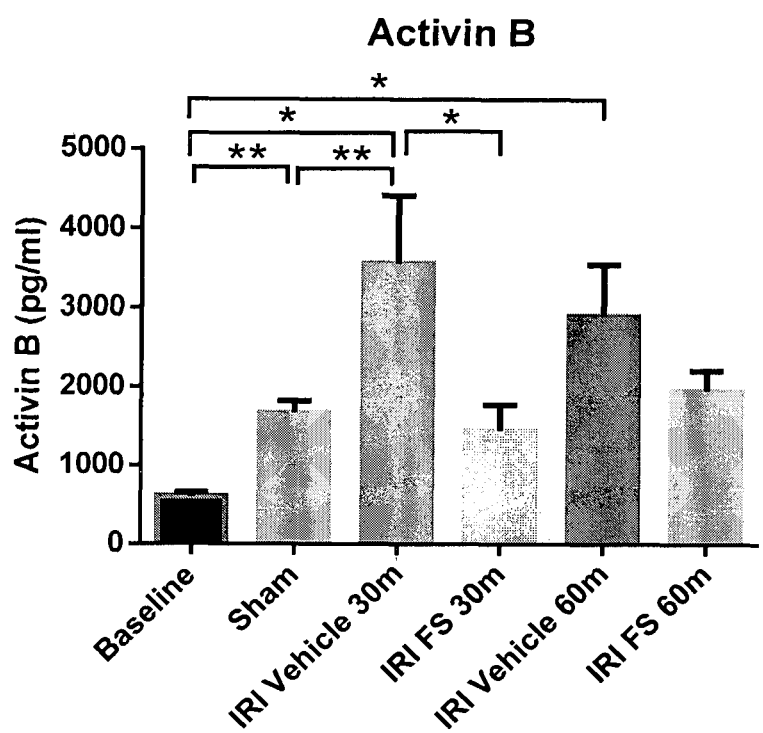
FIG. 13: Serum activin B protein levels following renal ischemia-reperfusion injury (IRI) in mouse. Serum activin B protein levels in baseline, sham and IRI groups 24 hrs after IRI as measured by ELISA. Mice in IRI groups were further divided into treatment groups receiving IP administration of either vehicle or follistatin (FS, 5 μg/mouse) 30 mins (30 m) or 60 mins (60 m) prior to IRI. Note the increase in activin B between basal and sham operated mice, indicative of a stimulus associated with surgery. Activin B levels are also significantly and markedly elevated by IRI in the vehicle treated mice and these increases are decreased in both groups of mice treated with follistatin at 30 (p<0.05) and 60 minutes before the IRI. Data are mean±SEM; N=4-6 mice per group; * p<0.05, ** p<0.01.
Figure 14:
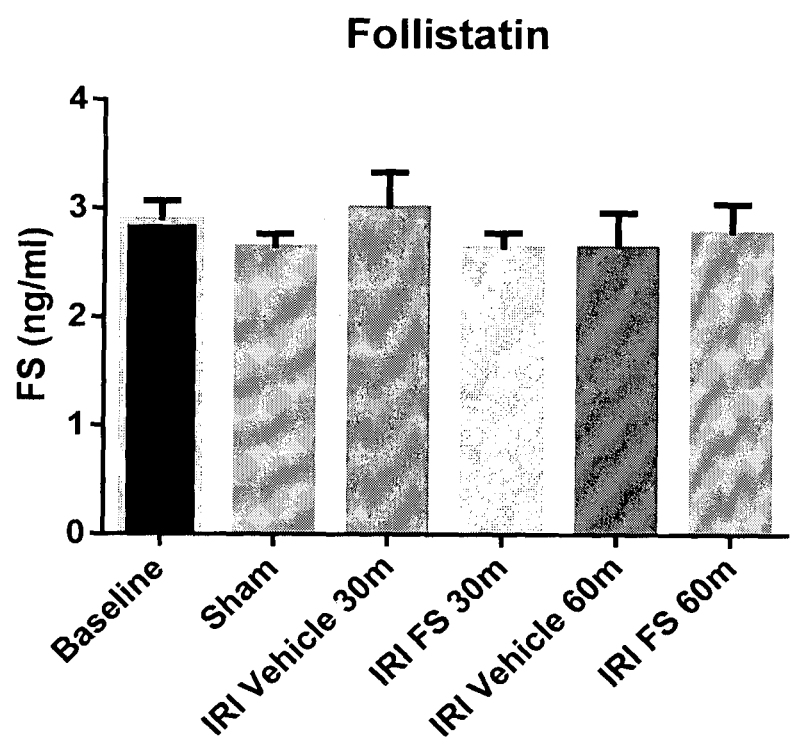
FIG. 14: Serum follistatin protein levels following renal ischemia-reperfusion injury (IRI) in mouse. Serum follistatin protein levels in baseline, sham and IRI groups 24 hrs after IRI as measured by MA. Mice in IRI groups were further divided into treatment groups receiving IP administration of either vehicle or follistatin (FS, 5 μg/mouse) 30 mins (30 m) or 60 mins (60 m) prior to IRI. The follistatin levels were not significantly changed in any group despite some groups of mice receiving follistatin. This is consistent with the small effective dose of follistatin administered to certain groups of mice. Data are mean±SEM; N=4-6 mice per group.

Results:

Effect of Follistatin Pretreatment on Serum Activin A, Activin B and Follistatin Levels Serum protein levels of activin A, activin B and follistatin 24 hrs after renal IRI in mice are shown in Table 5 and FIGS. 12 to 14.

There is an increase in the levels of activin A and B resulting from the unilateral nephrectomy alone as shown by comparing basal versus sham data, possibly reflecting the response of activin A and follistatin to surgical stress. Both activin A and B protein levels further increased as a result of the IRI (compare sham levels to IRI vehicle 30 m and 60 m). However, pretreatment with follistatin either 30 or 60 mins before IRI suppressed the IRI-induced increase in activin A and B levels, with significance observed for activin B levels at 30 mins pretreatment. Changes in serum follistatin levels were not observed. The data show that pretreatment with follistatin downregulates activin levels, which are increased as a result of IRI.

Effect of Follistatin Pretreatment on Renal Injury

Figure 15:
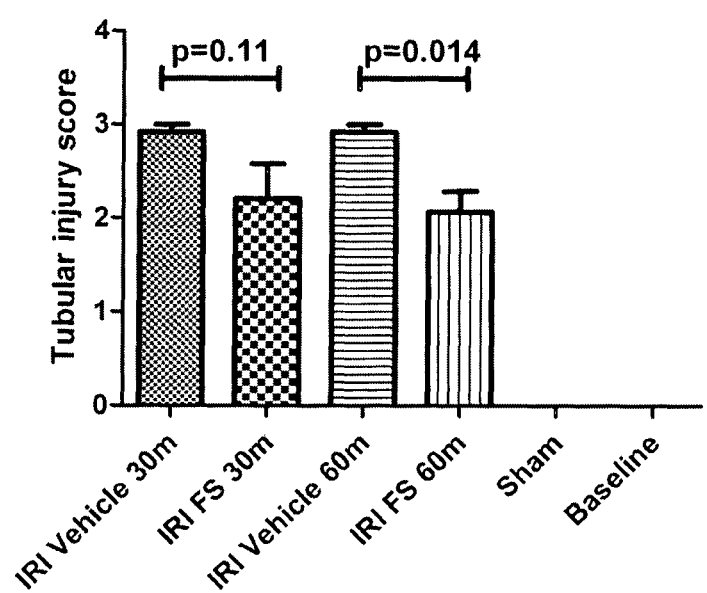
FIG. 15: Tubuar Injury Score following ischemia-reperfusion injury (IRI) in mice. Kidneys from mice treated with either vehicle or follistatin (FS, 5 μg/mouse administered IP) were removed 24 hrs after reperfusion, fixed and sectioned and the level of injury scored as 0=0%; 1=1-25%; 2=26-50%; 3=51-75%; 4>75%. Sham samples were taken from mice that had nephrectomy but not IRI; IRI samples are from mice that had ischemia-reperfusion injury; 30 m: administered 30 mins before IRI; 60 m: administered 60 mins before IRI. Note that the IRI produced a significant tubular injury that was reduced, but not significantly, by the administration of follistatin 30 minutes before IRI and significantly when the follistatin was administered 60 minutes before the IRI. Data are mean f SEM; N=4-6 mice per group.

The extent of injury on the kidney (tubular injury score) was assessed histologically by experienced nephrologists and the results provided in FIG. 15. The data show that the 20 mins ischemia caused injury to about 51-75% of the kidney (equating to a tubular injury score of 3). However, administration of follistatin prior to IRI reduced the extent of the injury, with scores representative of 26-50% tubular injury observed, and significance obtained with the 60 min pretreatment time.

Effect of Follistatin Pretreatment on Serum Creatinine Levels

Figure 16:
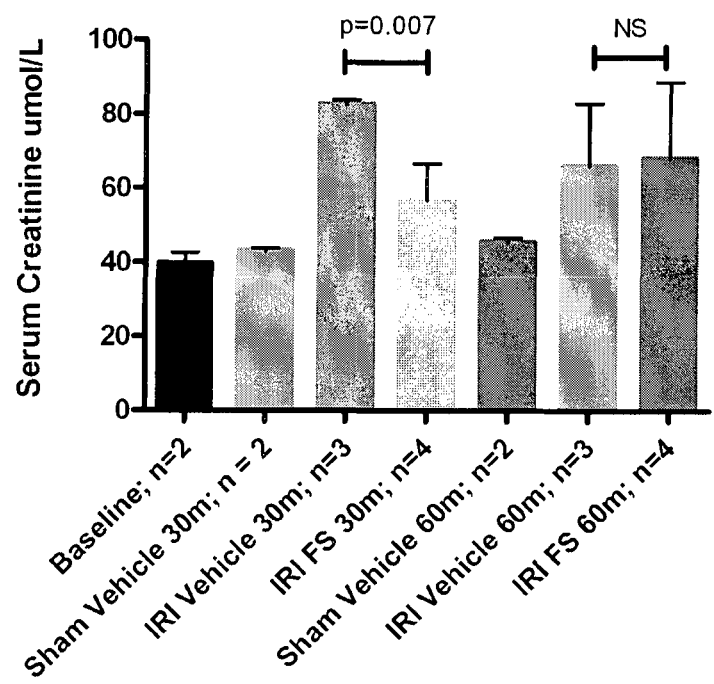
FIG. 16: Serum creatinine levels in mice following ischemia-reperfusion injury. Serum creatinine protein levels in baseline, sham and IRI groups 24 hrs after IRI as measured by creatinine assay kit (Abcam). Mice in IRI groups were further divided into treatment groups receiving IP administration of either vehicle or follistatin (FS, 5 μg/mouse) 30 mins (30 m) or 60 mins (60 m) prior to IRI. Note the elevated levels of creatinine in the IRI Vehicle groups and the significant decline in the tubular injury score in the mice given follistatin 30 minutes before the IRI. The serum creatinine levels were not significantly decreased in the mice given follistatin 60 minutes before the IRI. Data are mean±SEM. The numbers of mice in each experimental group are indicated. NS, non significant.

Serum creatinine is an important indicator of renal health. An elevation in serum creatinine levels is only observed when marked damage to the kidney occurs. Serum creatinine levels were measured in mice 24 hrs after IRI (FIG. 16). The data show that creatinine levels are elevated as a result of the 20 min ischemia (compare IRI vehicle levels to sham and baseline levels), indicative of kidney damage. Follistatin pretreatment significantly reduced the IRI-induced creatinine levels, particularly when administered 30 mins before IRI. This data shows that pretreatment with follistatin reduces the ischemia injury to the kidney, as measured by serum creatinine levels.

Conclusions:

The results demonstrate that follistatin can modulate the IRI response as judged by the modulation in both activin A and B levels. In addition follistatin reduces the amount of renal injury post ischemia-reperfusion as evidenced both biochemically (creatinine levels) and histologically (tubular injury score). Example 9—Lung IRI in dogs Design: Lung transplantation has become an emerging treatment for patients with end-stage lung disease. During a transplant the donor lung is clamped at the pulmonary artery and hilum and removed from the donor; it experiences a period of ischemia, and then is later transplanted into the recipient, where it undergoes reperfusion. Ischemia followed by reperfusion can lead to lung injury (ischemia-reperfusion injury or IRI), characterized by non-cardiogenic pulmonary oedema, inflammatory infiltrates, and hypoxia, and is unrelated to organ rejection. To minimise the IRI, the donor lung is often preserved by perfusing with a pneumoplegia solution during transience between the donor and recipient. In pulmonary models of IRI, the lung is subjected to ischemia for varying periods of time before circulation is re-established; thus, a mock transplant is performed. Ischemia is induced by completely clamping off the lung at the pulmonary artery and hilum and perfusing the lung with pneumoplegia solution. After the period of ischemia has lapsed, the pneumoplegia solution is flushed out, and the clamp is removed to allow blood to recirculate back into the lung, simulating what would be done during a transplant operation, without the surgical resection and subsequent implant of the lung. In this model, the organ preservation properties of pneumoplegia solutions can be tested and translated into the clinic as a mode of treating/preserving a harvested organ.

Experimental Procedure:

Two greyhound dogs were used in this experiment which was similar to that described in Sunose et al. (2001 *J Surg Res* 95:167-173). Briefly, the dogs were anesthetised and vital signs were monitored. The measurements in the right lung were used as the reference measurements for a healthy lung for each dog. The chest was opened and the left lung clamped at the pulmonary artery hilum using two clamps to ensure complete occlusion. The left lung was then perfused with pneumolplegia solution. About 1400 ml total volume was required to completely perfuse the lung. The efficiency of this was assessed by visualising the colour change from a dark pink colour to a pale coloured lung and confirmed by observing the clear perfusion effluent from pulmonary veins when the lung was flushed prior to reperfusion. One dog (dog 4) received standard pneumoplegia solution (Perfadex® with glutamine, calcium chloride and tromethamine buffer); the second dog (dog 5) received follistatin pneumoplegia solution (standard pneumoplegia solution with 500 µg/L follistatin-288). The chest was then closed and the lung maintained at 38° C. for a total ischemic time of 1 hr. The lung was then flushed with warm Ringer's solution before removing the clamp, allowing the reperfusion of blood back into the lung, and ventilating the lung with air. The right lung was then clamped and the dog was monitored while ventilation was maintained on the reperfused lung. The experiment was ceased 4 hrs after reperfusion or earlier if the injury was too severe resulting in lung or heart failure.

Results:

Physiological parameters which are indicative of lung function, from both dogs are displayed in Table 6.

The results show that Dog 4, which received standard pneumoplegia solution died at 40 mins post reperfusion due to pulmonary oedema and hypoxic left ventricular failure, the latter causing cardiac arrest. The very high pulmonary capillary wedge pressure (26 mmHg) observed in the injured lung 30 mins after reperfusion was causative to the pulmonary oedema. The declined cardiac output, mixed venous $O_2$ saturation at 41% (greater than 60% is considered healthy and normal), and no change in central venous pressure suggested that the failure of the heart was due to hypoxic left ventricular failure. In essence, the data show that the 1 hr ischemia caused severe injury to the lung, resulting in heart failure due to severe hypoxia and pulmonary oedema.

Dog 5, on the other hand, received pneumoplegia solution with follistatin (@500 µg/ml) and survived the ischemia-reperfusion for up to 4 hrs, after which the dog was selectively infused with a drug, phenobarbitone, to deepen anesthesia and stop the heart. Unlike dog 4, all physiological parameters of the reperfused lung in Dog 5 remained steady and similar to those of the normal lung throughout the duration of the study. Only the pulmonary vascular resistance (PVR) appeared to increase over time. This is because PVR is calculated as the pressure gradient across the lung divided by the cardiac output. In the case for Dog 5, pressure gradient remained constant while cardiac output slowly declined, hence the increase in PVR. It is important to note that the measured cardiac output, although declining, was considered normal and due to the nature of the anaesthetic used on the dog. Together, the parameters in Table 6 constitute a very thorough evaluation of function in the ischemia-reperfused lung and the resultant dysfunction for the cardiovascular system in Dog 4.

The predominant difference between Dog 4 and Dog 5 is the follistatin added to the pneumoplegia solution used in Dog 5. The data in Table 6 show that in absence of follistatin, the ischemia-induced injury was too severe for the lung to recover with physiological parameters indicative of a damaged lung (reduced lung compliance, elevated alveola dead space and elevated percentage lung shunt). However, when the injured lung was treated with follistatin, the physiological measurements after reperfusion were very similar to the respective right (control or uninjured) lung, suggesting that follistatin treatment minimised the injury to the lung.

Conclusion:

The data in Table 6 clearly show that treating the lung with follistatin during the period of ischemia minimises the damage incurred as a result of ischemia followed by reperfusion and improves lung function after repfusion.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

Numbers of patients undergoing lung transplantation, their cohort stratification, whether they received a lung transplant from a DCD donor and whether they were randomised to ischemic pre-conditioning during the transplant procedure.

| Diagnosis | Donor Clinically Dead? | Conditioning? | Number |
|---|---|---|---|
| Obstructive CF | Yes | Yes | 2 |
| | Yes | No | 3 |
| | No | Yes | 5 |
| | No | No | 1 |
| Restrictive | Yes | Yes | 1 |
| | Yes | No | 3 |
| | No | Yes | 4 |
| | No | No | 2 |

TABLE 1-continued

Numbers of patients undergoing lung transplantation, their cohort stratification, whether they received a lung transplant from a DCD donor and whether they were randomised to ischemic pre-conditioning during the transplant procedure.

| Diagnosis | Donor Clinically Dead? | Conditioning? | Number |
|---|---|---|---|
| Obstructive non-CF | Yes | Yes | 5 |
| | Yes | No | 3 |
| | No | Yes | 8 |
| | No | No | 11 |

TABLE 2

Activin A and follistatin concentrations, expressed as mean and 95% confidence limits, in normal adults, and patients undergoing lung transplantation.

| Cohort | Activin A (ng/ml) | Follistatin (ng/ml) |
|---|---|---|
| Normal | 0.108 (0.101-0.114) | 12.74 (11.95-13.52) |
| Obstructive CF | 0.221 (0.097-0.345)** | 11.39 (8.61-14.16) |
| Restrictive | 0.257 (0.152-0.437)*** | 12.16 (6.77-17.55) |
| Non-obstructive CF | 0.296 (0.121-0.351)** | 12.25 (9.78-14.72) |

**$P < 0.01$;
***$P < 0.001$ versus normal range (Mann-Whitney test).

TABLE 3

Serum levels of activin A and follistatin in pigs undergoing renal transplants. Data are presented as mean +/− SEM concentrations from 14 animals.

| | Time after induction of anesthesia (hours) | | | | |
|---|---|---|---|---|---|
| Analyte | 0 | 1 | 2 | 6 | 24 |
| Activin A (ng/ml) | 0.094 ± 0.006 | 0.465 ± 0.055*** | 0.057 ± 0.004 | 0.046 ± 0.005 | 0.127 ± 0.058 |
| Follistatin (ng/ml | 3.9 ± 0.5 | 74.6 ± 5.7*** | 15.2 ± 3.5 | 14.9 ± 1.9 | 19.4 ± 6.3* |

*$P < 0.05$;
***$P < 0.0001$ versus 0 timepoint (One-way analysis of variance).

TABLE 4

Serum activin A and follistatin concentrations in patients undergoing liver transplantation, relative to induction of anesthesia (mean +/− sem).

| | Activin A (N = 11) (ng/ml) | Follistatin (N = 11) (ng/ml) |
|---|---|---|
| Induction | 0.417 +/− 0.0 61 | 10.77 +/− 1.2 |
| Reperfusion | 0.350 +/− 0.072 | 9.83 +/− 1.0 |
| D1 | 0.188 +/− 0.021 | 11.0 +/− 1.0 |
| D3 | 0.190 +/− 0.026 | 5.66 +/− 0.6 |
| D7 | 0.220 +/− 0.040 | 6.46 +/− 0.3 |

TABLE 5

| | Baseline (n = 4) | Sham (n = 6) | IRI Vehicle 30 mins (n = 4) | IRI Follistatin 30 mins (n = 4) | IRI Vehicle 60 mins (n = 4) | IRI Follistatin 60 mins (n = 5) |
|---|---|---|---|---|---|---|
| Activin A | 40.3 +/− 6.1 | 84.9 +/− 6.2 | 254.5 +/− 42.3 | 156.2 +/− 42.3 | 259.2 +/− 47 | 197.2 +/− 38 |
| Activin B | 604.4 +/− 52.9 | 1666.5 +/− 157.4 | 3553.7 +/− 85.5 | *1438.5 +/− 329.6 | 2894.7 +/− 649.9 | 1953.8 +/− 250.5 |
| Follistatin | 2.88 +/− 0.18 | 2.63 +/− 0.13 | 3.0 +/− 0.33 | 2.63 +/− 0.15 | 2.63 +/− 0.33 | 2.77 +/− 0.27 |

*Significantly different to IRI Vehicle 30 mins, $p < 0.05$

TABLE 6

Physiological indicators of right (control) lung and left (ischemia-induced injury) lung

| Physiological Paramaters** | Dog 4 (standard pneumoplegia solution) | | Dog 5 (follistatin pneumoplegia soluton) | | | | | |
|---|---|---|---|---|---|---|---|---|
| | *right lung 30 min | *left lung 30 min | *right lung 30 min | *left lung 30 min | *left lung 1 hr | *left lung 2 hr | *left lung 3 hr | *left lung 4 hr |
| lung compliance (ml/mmhg) | 27.55 | 17.81 | 27.00 | 28.10 | 28.50 | 29.80 | 29.50 | 28.08 |
| alveola deadspace as percentage of tidal volume (%) | 13.6 | 47.65 | 19.78 | 15.43 | 10.30 | 18.47 | 13.64 | 7.94 |
| lung shunt as percentage of cardiac output (%) | 7.4 | 86.65 | 11.65 | 11.32 | 7.07 | 13.16 | 7.71 | 7.21 |
| pulmonary vascular resistance (dyn · sec · cm$^{-5}$) | 105.6 | 137.3 | 181.33 | 192.24 | 210.16 | 198.17 | 199.62 | 302.22 |
| mean pulmonary artery pressure (mmHg) | 16 | 34 | 26 | 24 | 27 | 26 | 24 | 22 |
| Pulmonary capillary wedge pressure (mmHg.) | 7 | 26 | 9 | 11 | 11 | 10 | 10 | 7 |
| trans-pulmonary gradient (mmHg) | 9 | 8 | 17 | 16.1 | 15 | 19 | 13 | 17 |
| heart Rate (beats/min) | 110 | 210 | 168 | 120 | 132 | 140 | 92 | 108 |
| systemic blood pressure (mmHg) | 126 | 77 | 95 | 82 | 88 | 111 | 114 | 110 |
| central venous pressure (mmHg) | 6 | 5 | 6 | 8 | 7 | 7 | 6 | 6 |
| noradrenaline infusion (ug/min) | 0.6 | 8 | 1.3 | 1.3 | 1.3 | 1.3 | 0.6 | 0.6 |
| adrenaline infusion (ug/min) | 0 | 0 | 2 | 2 | 2 | 1 | 1 | 1 |
| cardiac output (l/min) | 6.82 | 4.66 | 7.5 | 6.7 | 5.71 | 7.67 | 5.21 | 4.5 |
| mixed venous O2 saturation (%) | 84 | 41 | 73.91 | 68.17 | 61.60 | 69.51 | 69.18 | 65.25 |
| systemic arterial PO2 (mmHg) | 121 | 38 | 72 | 69 | 72 | 65 | 82 | 81 |
| arterial oxygen saturation | 98.41 | 60.14 | 94.54 | 93.89 | 94.54 | 92.83 | 96.05 | 95.93 |

*Note: right lung is normal lung (control lung) and measurements were taken 30 mins after left lung was clamped; left lung is ischemia lung and time indicates time after reperfusion (t = 0 is when right lung was clamped).
**Explanation of parameters in table:
Lung compliance: is a measure of the ease of expansion of the lungs and thorax, determined by pulmonary volume and elasticity. A high compliance is consistent with a healthy lung. Decreased compliance means that the lung is much harder to inflate and a greater change in pressure is needed for a given change in volume, as in atelectasis, oedema, fibrosis, pneumonia, or absence of surfactant.
Alveolar dead space as a percentage of tidal volume: is the portion of inhaled air that reaches the alveoli (airsacs in the lung) but does not undergo gas exchange as the alveoli have little or no blood flowing through their adjacent pulmonary capillaries, i.e., alveoli that are ventilated but not perfused, and where, as a result, no gas exchange can occur.
Lung shunt as a percentage of cardiac output: this is a physiological condition which results when the alveoli of the lungs are perfused with blood as normal, but ventilation (the supply of air) fails to supply the perfused region. A pulmonary shunt often occurs when the alveoli fill with fluid, causing parts of the lung to be unventilated although they are still perfused. When expressed as a percentage of cardiac output, the value represents the percentage of blood put out by the heart that is not completely oxygenated.
Pulmonary vascular resistance (PVR): this is calculated as the pressure gradient across the lung (mean pulmonary artery pressure minus left atrial pressure) divided by the cardiac output. Note: this is not perceived as a reliable measure on its own as it relies on the invalid assumptions that (i) blood is a Newtonian fluid, (ii) the pulmonary resistance vessels are unbranched small rigid tubes of circular surface sections, and (iii) pulmonary blood flow is streamlined and non-pulsatile. In addition, the lung vessels are able to dilate or constrict (when blood flow through the lung increases or decreases). Therefore, we cannot assume that changes in PVR are necessarily indicative of lung damage, and so the PVR can give misleading information under conditions of changing cardiac output.
Mean pulmonary artery pressure: the pressure in the pulmonary artery leading to the lungs. It also allows for indirect measurement of left heart pressures since the pulmonary veins have no valves in them and collects the information needed to calculate cardiac output and resistance.
Pulmonary capillary wedge pressure: this provides a measure of the left atrial pressure (oxygenated blood from the pulmonary veins into the left atrium). Pulmonary capillary pressure (Pcap) is the predominant force that drives fluid out of the pulmonary capillaries into the interstitium. Increasing hydrostatic capillary pressure is directly proportional to the lung's transvascular filtration rate, and in the extreme leads to pulmonary oedema. In the dog, an increase of 15-20 mmHg above normal results in oedema.
Trans-pulmonary gradient: mean pulmonary artery pressure minus pulmonary capillary wedge pressure.
Heart rate: Dog 4 had extremely high heart rate after reperfusion - an indicator that the heart was under a lot of stress as a result of the extreme hypoxia in the blood caused by the lung injury. The right side of the heart was more tolerant to these conditions.
Systemic blood pressure: the pressure exerted by circulating blood upon the walls of blood vessels.
Central venous pressure (CVP): a good approximation of right atrial pressure. CVP reflects the amount of blood returning to the heart and the ability of the heart to pump the blood into the arterial system.
Noradreniline and adrenaline infusion: Noradrenaline and adrenaline are cardiac stimulants (also known as inotropes). They are used to boost cardiac output when it is too low.
Cardiac output: is the volume of blood being pumped from the heart in the time interval of 1 minute.

TABLE 6-continued

Physiological indicators of right (control) lung and left (ischemia-induced injury) lung

|  | Dog 4 (standard pneumoplegia solution) | | Dog 5 (follistatin pneumoplegia soluton) | | | | | |
| --- | --- | --- | --- | --- | --- | --- | --- | --- |
| Physiological Paramaters** | *right lung 30 min | *left lung 30 min | *right lung 30 min | *left lung 30 min | *left lung 1 hr | *left lung 2 hr | *left lung 3 hr | *left lung 4 hr |

Mixed venous O2 saturation: is the percentage of oxygen bound to hemoglobin in blood returning to the right side of the heart. This reflects the amount of oxygen left in the blood after the tissues remove what they need. It is an indication of when a patient's body is extracting more oxygen than normally. An increase in extraction is the body's way to meet tissue oxygen needs when the amount of oxygen reaching the tissues is less than required.
Systemic arterial PO2: the O2 pressure in the blood leaving the lungs.
Arterial oxygen saturation: the percentage of oxygen in the blood leaving the lungs (will be close to 100% in normal healthy lung).

BIBLIOGRAPHY

Bittner et al. (2006) *Eur J Cardiothorac Surg* 29:210-215
Boros and Bromberg (2006) *Am J Transplant* 6:652-658
Bunin et al. (1994) *Proc Natl Acad Sci USA* 91:4708-4712
Cash et al (2012) *Mol. Endocrinol.* 26 (7): 1167-1178
Chalk et al. (2004) *Biochem Biophys Res. Commun* 319: 264-274
Chong et al. (2004) *J Thorac Cardiovasc Surg* 128:170-179.
Christie et al. (2005) *Am J Respir Crit Care Med* 171:1312-1316
Christie et al. (2005) *Chest* 127:161-165
Conrad et al. (1995) *Mol Div* 1:69-78
Cui et al. (2004) *Comput Methods Programs Biomed* 75:67-73
de Perrot et al. (2003) *Am J Respir Crit Care Med* 167:490-511
DeWitt et al. (1993) *Proc Natl Acad Sci USA*, 90:6909-6913
Ding & Lawrence (2001) *Nucl Acids Res* 20:1034-1046
Ding & Lawrence (2003) *Nucl Acids Res* 31: 7280-7301
Ding et al. *Nucleic Acids Res* 32 Web Server issue, W135-W141
Douillard and Hoffman (1981), Basic Facts about Hybridomas, in *Compendium of Immunology* Vol II, ed. by Schwartz
Egleton (1997) *Peptides* 18:1431-1439.
Elbashir et al. (2002) *Methods* 26: 199-213
Ellington (1994) *Curr Biol* 4:427-429 Estenne and Hertz (2002) *Am J Respir Crit Care Med* 166:440-444
Estenne et al. (2002) *J Heart Lung Transplant* 21:297-310
Hausenloy & Yellon (2011) *Nat Rev Cardiol* 8:619-629
Jamieson and Friend (2008) *Front Biosci* 13:221-235
Keutman et al. (2004) *Mol Endocrinol* 18(1):228-240
Khvorova et al. (2003) *Cell* 115:209-216
Klein et al. (1991) *Endocrinology*, 128:1048-1056
Klug et al. (1994) *Mol Biol Reports* 20:97-107
Knight et al. (1996) *J Endocrinol* 148:267-279
Kohler and Milstein (1975) *Nature* 256: 495-499
Kozower et al. (2003) *Nat Biotechnol* 21:392-398
Lande et al. (2007) *Proc Am Thorac Soc* 4:44-51
Langer (1990) *Science* 249:1527-1533
Laskowski et al. (2000) *Ann Transplant* 5:29-35
Lato et al. (1995) *Chem Biol* 2:291-303
Lim et al. (2010) *ANZ J Surg* 80:265-270
Lu et al. (2006) *Chest* 130:847-854
Ludlow et al. (2009) *Clin Endocrinol* 71:867-873
Mori et al. (2007) *Eur J Cardiothorac Surg* 32:791-795
Ng et al. (2005) *Eur Respir J* 25:356-363
O'Connor et al. (1999) *Hum Reprod* 14:827-832
Okada et al. (2001) *Faseb J* 15:2757-2759
Reynolds et al. (2004) *Nat Biotechnol* 22:326-330
Robertson et al. (1987) *Biochem Biophys Res Commun* 149:744-749
Schwarz, et al. (2003) *Cell* 115:199-208
Shimoyama et al. (2005) *Eur J Cardiothorac Surg* 28:581-587
Stein and Cohen (1988) *Cancer Res* 48:2659-2668
Struber et al. (2007) *J Thorac Cardiovasc Surg* 133:1620-1625
Sunose, et al. (2001) *J Surg Res* 95:167-173
Uphoff et al. (1996) *Curr Opin Struct Biol* 6:281-287
van der Krol et al. (1988) *Biotechniques* 6:958-976
van der Woude et al. (2004) *J Investig Med* 52:323-329
Venardos et al. (2009) *J Cell Biochem* 108:156-168
Wallis et al. (1995) *Chem Biol* 2:543-552
Wang et al. (2004) *Bioinformatics* 20:1818-1820
Wei et al. (1999) *Circ Res* 85:682-689
Winnall et al. (2009) *Mol Cell Endocrinol* 307:169-175
Zhai et al. (2006) *Transplant Proc* 38:3369-3371

The invention claimed is:

1. A method of reducing the onset or progression of mammalian graft tissue dysfunction in a graft recipient in need thereof, comprising administering follistatin to:
   (a) a graft donor prior to graft tissue removal;
   (b) a graft tissue before its removal from the donor; or
   (c) a graft tissue subsequent to its removal from the donor but prior to or at the time of its transplantation in the recipient,
   in an amount effective to downregulate the functional level of activin or upregulate the functional level of follistatin in the graft tissue
   wherein the method is effective to reduce the onset or progression of mammalian graft tissue dysfunction in the graft recipient.

2. A method for treating mammalian graft tissue dysfunction in a graft recipient in need thereof comprising administering follistatin to:
   (a) a graft donor prior to graft tissue removal;
   (b) a graft tissue before its removal from the donor; or
   (c) a graft tissue subsequent to its removal from the donor but prior to or at the time of its transplantation in the recipient,
   in an amount effective to downregulate the functional level of activin or upregulate the functional level of follistatin in the graft tissue,
   wherein the method is effective to reduce the onset or progression of mammalian graft tissue dysfunction in the graft recipient.

3. The method according to claim 1, wherein said graft tissue is selected from the group consisting of lung, kidney, liver and heart.

4. The method according to claim 1, wherein said mammalian graft tissue is human tissue.

5. The method according to claim 1, wherein said follistatin is FS315 or FS288.

6. The method according to claim 1, wherein said follistatin is selected from the group consisting of
   (i) FS288 or FS315;
   (ii) wild-type follistatin-like 3 protein (FSTL3);
   (iii) a follistatin analogue having the structure ND-FSD1-FSD2;
   (iv) an analogue of (i) or (iii) with FSD1 substituted by FSD1', where FSD1' represents FSD1 with the heparin-binding site removed;
   (v) an analogue of (i) or (iii) with FSD1 substituted by FSD1*, where FSD1* represents FSD1 with the sequence prior to and including the heparin-binding sequence removed;
   (vi) a hybrid form of (i) or (iii) where at least one of the domains is substituted by a corresponding FSTL3 domain N3D, FS3D1, FS3D2 and FS3D3; and
   (vii) a hybrid form of (ii) where at least one of the domains is substituted by a corresponding FS domain ND, FSD1, FSD1', FSD1* and FSD2.

7. The method according to claim 6, wherein said follistatin analogue having the structure ND-FSD1-FSD2 (iii) is wild-type minus FSD3.

8. The method according to claim 1, wherein said follistatin is administered to the graft tissue at the time of transplantation.

9. The method according to claim 1, wherein said graft tissue is lung.

* * * * *